US012703863B2

(12) United States Patent
Mihailescu et al.

(10) Patent No.: US 12,703,863 B2
(45) Date of Patent: Aug. 11, 2026

(54) RNA G-QUADRUPLEX STRUCTURE IN PRE-miRNA-1229 AS A THERAPEUTIC TARGET FOR ALZHEIMER'S DISEASE AND VARIOUS CANCERS

(71) Applicant: DUQUESNE UNIVERSITY OF THE HOLY SPIRIT, Pittsburgh, PA (US)

(72) Inventors: Mihaela Rita Mihailescu, Pittsburgh, PA (US); Joshua A. Imperatore, Canonsburg, PA (US)

(73) Assignee: DUQUESNE UNIVERSITY OF THE HOLY SPIRIT, Pittsburgh, PA (US)

( * ) Notice: Subject to any disclaimer, the term of this patent is extended or adjusted under 35 U.S.C. 154(b) by 0 days.

(21) Appl. No.: 17/301,835

(22) Filed: Apr. 15, 2021

(65) Prior Publication Data

US 2021/0340537 A1 Nov. 4, 2021

Related U.S. Application Data

(60) Provisional application No. 63/010,175, filed on Apr. 15, 2020.

(51) Int. Cl.
*C12N 15/113* (2010.01)

(52) U.S. Cl.
CPC .... *C12N 15/113* (2013.01); *C12N 2310/3181* (2013.01); *C12N 2310/322* (2013.01); *C12N 2320/34* (2013.01)

(58) Field of Classification Search
CPC .......... C12N 15/113; C12N 2310/3181; C12N 2310/322; C12N 2310/113
See application file for complete search history.

(56) References Cited

U.S. PATENT DOCUMENTS

2019/0231809 A1 * 8/2019 Artero Allepuz .... C12N 15/113

FOREIGN PATENT DOCUMENTS

WO WO-2014179765 A2 * 11/2014 ........... C12Q 1/6883

OTHER PUBLICATIONS

Sugiyama and Kattaka, Chiral Peptide Nucleic Acids with a Substituent in the N-(2-Aminoethy)glycine Backbone, 2013, Molecules, 18, 287-310 (Year: 2013).*

Martin-Pintado et al., The solution structure of double helical arabino nucleic acids (ANA and 20F-ANA): effect of arabinoses in duplex-hairpin interconversion, 2012, Nucleic Acids Research, 40, 9329-9339. (Year: 2012).*

Monia et al., Selective inhibition of Mutant Ha-ras mRNA expression by antisense oligoucleotides, J. Biol. Chem., 1992, p. 19954-19962 (Year: 1992).*

Krutzfeldt et al., Specificity, duplex degradation and subcellular localization of antagomirs, Nucleic Acids Research, 2007, 2885-2892. (Year: 2007).*

Amakiri et al., Amyloid Beta and MicroRNAs in Alzheimer's Disease, 2019, Front. Neurosci., 13, p. 1-10. (Year: 2019).* mirbase.org/hairpin/MI0006319#hsa-miR-1229-5p, accessed Nov. 7, 2024 (Year: 2024).*

Fay et al. RNAG-Quadruplexes in Biology: Principles and Molecular Mechanisms, 2017, J. of Mol. Biology, 429, p. 2127-2147. (Year: 2017).*

Imperatore et al., Characterization of a G-Quadruplex Structure in Pre-miRNA-1229 and in Its Alzheimer's Disease-Associated Variant rs2291418: Implications for miRNA-1229 Maturation, Jan. 2020, Int. J. Mol. Sci., 21, 1-18. (Year: 2020).*

Stenvang and Kauppinen, MicroRNAs as targets forantisense-based therapeutics, 2008, Expert Opin. Biol. Ther., 8, 59-81. (Year: 2008).*

Armitage, B.A. (2019). Targeting G-Quadruplexes with PNA Oligomers, p. 333-345, In: Yang, D., Lin, C. (eds) G-Quadruplex Nucleic Acids. Methods in Molecular Biology, vol. 2035. Humana, New York, NY. https://doi.org/10.1007/978-1-4939-9666-7_2, (Year: 2019).*

Oyaghire et al., RNA G-Quadruplex Invasion and Translation Inhibition by Antisense γ-Peptide Nucleic Acid Oligomers, Biochemistry (2016), 55(13):1977-1988.

Souleimanian et al., Antisense 2'-Deoxy, 2'-FLUROARABINO Nucleic Acids (2'F-ANAS) Oligonucleotides: in Vitro Gymnotic Silencers of Gene Expression Whose Potency is Enhanced by Fatty Acids, Mol. Ther.—Nucleic Acids (2012), 1, E43.

Simone et al., G-Quadruplex-Binding Small Molecules Ameliorate C9ORF72 FTD / ALS Pathology In Vitro and In Vivo, EMBO Mol. Med. (2018), 10:22-31.

Ghanbari et al., The Role of Micrornas in Age-Related Disorders, Sci. Rep. (2016), 6:28387.

Souleimanian et al., "Antisense 2-Deoxy, 2-Fluoroarabino Nucleic Acid (2F-ANA) Oligonucleotides: In Vitro Gymnotic Silencersof Gene Expression Whose Potency Is Enhanced by Fatty Acids", Molecular Therapy-Nucleic Acids (2012) 1, e43; doi:10.1038/mtna.2012.35, published online Oct. 2, 2012.

Mihailescu, "Gene expression regulation: lessons from noncoding RNAs", downloaded from rnajournal.cshlp.org on Nov. 15, 2023—Published by Cold Spring Harbor Laboratory Press, RNA 2015 21: 695-696.

Kallweit, L., et al., Chronic RNA G-quadruplex accumulation in aging and Alzheimer's disease, eLife 2025;14: RP105446. DOI: https://doi.org/10.7554/eLife. 105446.

Bellina, A., et al., Apurinic/Apyrimidinic Endodeoxyribonuclease 1 modulates RNA G-quadruplex folding of miR-92b and controls its expression in cancer cells, PNAS 2024 vol. 121 No. 46, http://doi.org/10,1073/pans.2317861121.

Pandey, S., et al., The RNA Stem-Loop to G-Quadruplex Equilibrium Controls Mature MicroRNA Production inside the Cell, Biochemistry 2015, 54, 7067-7078.

(Continued)

*Primary Examiner* — Soren Harward
*Assistant Examiner* — Keyur A Vyas
(74) *Attorney, Agent, or Firm* — Debora Plehn-Dujowich; Eckert Seamans Cherin & Mellott, LLC

(57) ABSTRACT

Provided is an agent that binds to a wild type or variant pre-miRNA-1229 comprising a G-quadruplex (GQ) structure, wherein binding of the agent to the wild type or variant pre-miRNA-1229 stabilizes the GQ structure of the wild type or variant pre-miRNA-1229. In some embodiments, the variant is rs2291418. Provided is a method of treating a disease in a subject, comprising: administering a therapeutically effective amount of the agent to the subject. In some embodiments, the disease is Alzheimer's disease, cancer or coronary artery calcification.

2 Claims, 16 Drawing Sheets

Specification includes a Sequence Listing.

(56) References Cited

OTHER PUBLICATIONS

Liu, G. et al., RNA G-quadruplex regulates microRNA-26a biogenesis and function, Journal of Hepatology 2020 vol. 73 j 371-382.
Arachchilage, G. M., et al., Targeting of G-Quadruplex Harboring Pre-miRNA 92b by LNA Rescues PTEN Expression in NSCL Cancer Cells, ACS Chem. Biol. 2018, 13, 909-914.
Kharel, P. et al., Stress promotes RNA G-quadruplex folding in human cells, Nature Communications | ( 2023)14:205.

* cited by examiner

A
B
rs2291418

C

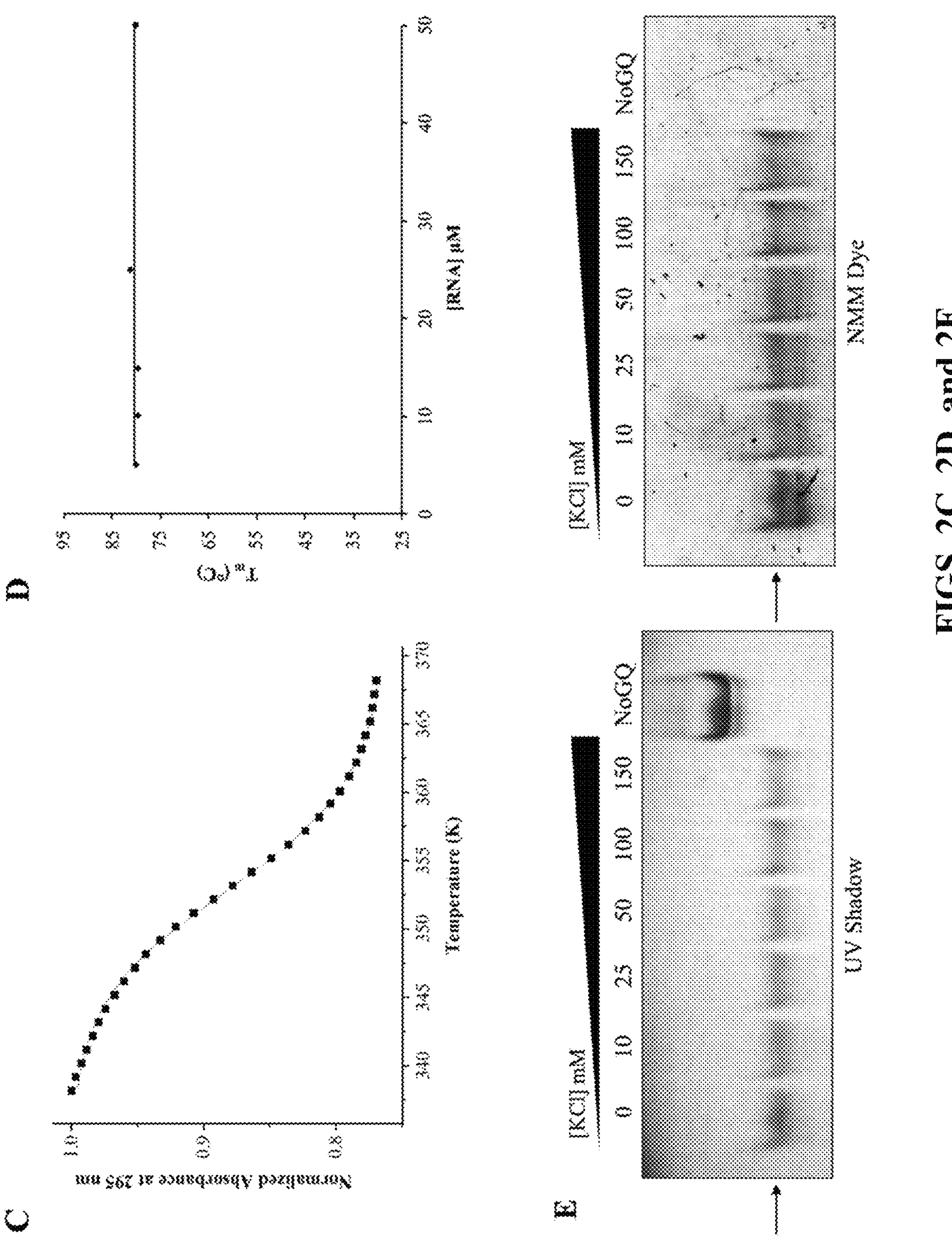
FIGS. 2C, 2D, and 2E

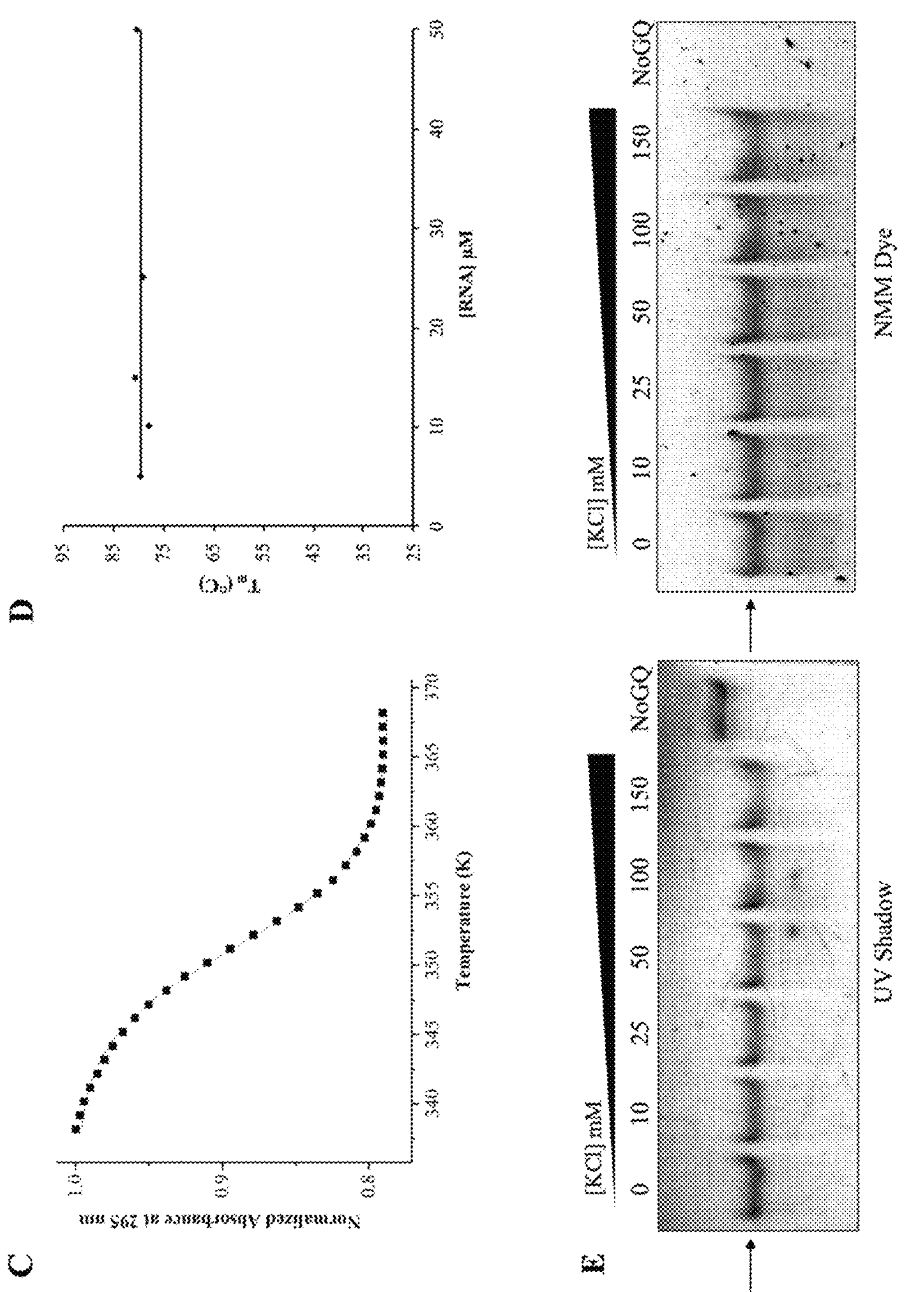
FIGS. 5C, 5D, and 5E

RNA G-QUADRUPLEX STRUCTURE IN PRE-miRNA-1229 AS A THERAPEUTIC TARGET FOR ALZHEIMER'S DISEASE AND VARIOUS CANCERS

CROSS-REFERENCE TO RELATED APPLICATIONS

This invention claims the benefit of U.S. Provisional Application No. 63/010,175 filed on Apr. 15, 2020, which is hereby incorporated by reference in its entirety.

GOVERNMENT SUPPORT

This invention was made with government support under grant 9R15GM127307-04 awarded by the National Institutes of Health (NIH). The government has certain rights in the invention.

SEQUENCE LISTING

The instant application contains a Sequence Listing which is submitted in ASCII format via EFS-Web and is hereby incorporated by reference in its entirety. The ASCII copy, created on Apr. 11, 2021, is named 049459-00489_SequenceListing and is 2,474 bytes in size.

FIELD

The invention relates to a G-quadruplex structure within pre-miRNA-1229 as a novel therapeutic target in Alzheimer's disease, cancer and other diseases, and methods of treating Alzheimer's disease, cancer and other diseases, as well as methods of mitigating the progression or precluding the onset of Alzheimer's disease, cancer and other diseases, by stabilizing or destabilizing the G-quadruplex structure to decrease or increase the production of mature miRNA-1229 to normal levels.

BACKGROUND

Alzheimer's disease (AD) is the most common age-related neurodegenerative disease, currently affecting an estimated 4.7 million people in the United States alone, with that number expected to nearly triple to a projected 13.8 million by the year 2050. The disease is characterized by cognitive declines such as progressive memory loss, confusion, and disorientation, as well as behavioral and mood changes. It is widely accepted that AD is also a leading cause of dementia in older individuals. At a molecular level, the development of AD can be associated with the accumulation of filamentous tau tangles inside of neurons and of beta amyloid (AD) plaques extracellularly. The accumulation of these proteins interferes with proper neuron-to-neuron communication at synapses in AD, resulting in disrupted communication of information and eventual cell death.

Aβ is generated by endoproteolytic cleavage into a 40-42 amino acid fragment from the transmembrane amyloid precursor protein (APP). While the main function of APP has not yet been determined, it is generally agreed upon that dysregulation of its processing is a major factor in the development of the neurotoxic Aβ deposits in AD. Many studies have determined that this may occur due to missense mutations within APP, resulting in an increased production of $A\beta_{42}$, the longer and more amyloidogenic variant that has an increased prevalence in AD patients. However, another possibility is that the dysregulation of various other proteins involved in this process may impair proper cleavage and trafficking of APP. Genome-wide association (GWAS) studies have determined a comprehensive list of genes associated with AD, including those that encode for apolipoprotein E (APOE), death-associated protein kinase 1 (DAPK1), interleukin 8 (IL8), transferrin, and sortilin-related receptor (SORL1). The latter of these proteins, SORL1, is a multifunctional membrane-bound receptor protein expressed throughout the brain that plays roles in cell-to-cell signaling and vesicle trafficking. Recent studies have reported that SORL1 functions to direct APP into recycling pathways under normal conditions. However, the downregulation of SORL1 expression results in APP being sorted into Aβ-generating pathways, demonstrating a potential mechanistic function of SORL1 in AD pathogenesis. Inherited genetic variants within SORL1 mRNA that are associated with AD have been shown to downregulate SORL1 protein translation. Additionally, other molecular mechanisms, such as microRNA (miRNA) dysregulation, have also been proposed to be involved in AD pathogenesis. miRNAs are a class of short, noncoding RNA approximately 20-24-nucleotides (nt) in length which bind to complementary "seed regions" within the 3' untranslated region (UTR) of mRNAs and regulate their translation. Mature miRNA is produced via a distinct biogenesis pathway, which begins with the transcription of miRNA genes to produce the primary miRNA (pri-miRNA), which is further processed by the ribonuclease III enzyme Drosha and the protein DiGeorge syndrome critical region 8 (DGCR8) into precursor miRNAs (pre-miRNA), 70-90-nt sequences that contain a 2-nt overhang on their 3' end. The pre-miRNAs, proposed to fold into extended hairpin structures, are exported to the cytoplasm in a Ran-GTP energy-driven process by the nucleocytoplasmic shuttling protein Exportin-5, which recognizes their 3' overhang. In the cytoplasm, the endoribonuclease III enzyme Dicer recognizes the pre-miRNA stem-loop structure, cleaving off the terminal loop and yielding an imperfect double-stranded miRNA:miRNA*duplex. Dicer further associates with various other proteins to formthe RNA-induced silencing complex (RISC), including Argonaute2(AGO2) andhuman immunodeficiency virus (HIV) transactivating response RNA (TAR) binding protein (TRBP). While the mature miRNA remains incorporated in the miRNA:RISC complex, the opposite strand, or passenger strand (miRNA*), is discarded. The miRNA-guided RISC complex subsequently recognizes and binds to mRNA targets, leading to mRNA cleavage and/or translational repression.

The importance of regulating miRNA levels has been demonstrated in a multitude of studies, with dysregulated levels being associated with various diseases, such as AD, Down syndrome, and many cancers. It has been proposed that the formation of alternative secondary structures in pre-miRNAs can affect their processing by Dicer and thus, mature miRNA production within the cell. Bioinformatics studies have concluded that 13-16% of all human pre-miRNA sequences contain guanine-rich (G-rich) regions that have the potential to form G-quadruplex (GQ) structures. GQs are non-canonical secondary structures formed by stacking of two or more cyclic, planar G-quartet arrangements of four guanine residues and stabilized by Hoogsteen-type hydrogen bonds, 7-7 stacking interactions, and intercalating monovalent cations. The formation of these GQ structures within G-rich pre-miRNAs has been proposed to inhibit their processing by Dicer due to the lack of a terminal stem loop.

Drugs are available to alleviate the symptoms of AD, however, there is no cure for AD, nor are there available drugs that treat the causes of AD. There have been attempts to discover a cure or drug to treat the causes of AD by targeting AD, which have resulted in adverse side effects such as brain edema and micro-hemorrhages. Thus, there is a need in the art to develop a mechanism for treating the causes of AD, mitigating the progression of AD, and precluding the onset of AD absent of adverse side effects.

SUMMARY OF THE INVENTION

Provided is an agent that binds to a wild type or variant pre-miRNA-1229 comprising a G-quadruplex (GQ) structure, wherein binding of the agent to the wild type or variant pre-miRNA-1229 stabilizes the GQ structure of the wild type or variant pre-miRNA-1229. In some embodiments, the variant is rs2291418.

In some embodiments, the agent comprises an engineered protein nucleic acid (PNA). In further embodiments, the PNA is a gamma PNA.

In some embodiments, the PNA or gamma PNA comprises a sequence selected from the group consisting of:

```
                                    (SEQ ID NO: 5)
AGCCCACGCUCUCCCCCAAA

                                    (SEQ ID NO: 6)
UGAACCCCAGCCCACGCUCU;
and

                                    (SEQ ID NO: 7)
GGGUGUCCCUGAACCCCAGC.
```

In some embodiments, the PNA or gamma PNA further comprises a C-terminal lysine residue and is selected from the group consisting of:

(SEQ ID NO: 5)
$H_2N$-Lys AGCCCACGCUCUCCCCCAAA-H (SEQ ID NO: 6)
$H_2N$-Lys UGAACCCCAGCCCACGCUCU-H;
and (SEQ ID NO: 7)
$H_2N$-Lys GGGUGUCCCUGAACCCCAGC-H.

In some embodiments the agent comprises 2'-deoxy 2'-fluoroarabino (2'-FANA) oligonucleotides. In further embodiments the 2'-FANA oligonucleotides comprise a sequence selected from the group consisting of:

```
                                    (SEQ ID NO: 8)
AGCCCACGCUCUCCCCCAAA

                                    (SEQ ID NO: 9)
UGAACCCCAGCCCACGCUCU;
and

                                   (SEQ ID NO: 10)
GGGUGUCCCUGAACCCCAGC.
```

In some embodiments, the agent comprises a small molecule.

Provided is a method of treating a disease in a subject, comprising: administering a therapeutically effective amount of the agent of any one of the previous embodiments to the subject. In some embodiments, the disease is Alzheimer's disease, cancer or coronary artery calcification. In further embodiments, the cancer is breast cancer or colorectal cancer.

Also provided is a composition comprising the agent of any one of the embodiments described herein.

Provided is a method of treating a disease in a subject, comprising: administering a therapeutically effective amount of the composition comprising the agent of any one of the embodiments described herein to the subject. In some embodiments, the disease is Alzheimer's disease, cancer or coronary artery calcification. In further embodiments, the cancer is breast cancer or colorectal cancer.

Provided is a novel therapeutic target for Alzheimer's disease in the form of a G-quadruplex structure that coexists in equilibrium with a canonical hairpin structure in the G-rich region of the pre-miRNA-1229 sequence.

Provided is a method for treating Alzheimer's disease, cancer, or other disease and mitigating their progression. In some embodiments, the other disease is coronary artery calcification. In further embodiments, the cancer is breast cancer or colorectal cancer. The method includes stabilizing or destabilizing a novel G-quadruplex structure in equilibrium with a canonical hairpin structure in the G-rich region of the pre-miRNA-1229 sequence, controlling the production of mature miRNA-1229-3p and subsequently regulating SORL1 protein. Further, rs2291418 SNP is located within the G-rich region of the pre-miRNA-1229 sequence. The stabilizing or destabilizing of the G-quadruplex structure includes the rs2291418 SNP being effective to change the equilibrium between the G-quadruplex structure and the canonical hairpin structure.

For Alzheimer's disease, the method includes stabilizing the G-quadruplex structure in equilibrium with the canonical hairpin structure, lowering the production of mature miRNA-1229-3p to a level corresponding to a normal level, and increasing the SORL1 protein to a level corresponding to a normal level.

Provided is a method of controlling miRNA dysregulation to reduce effects of Alzheimer's disease, cancer, or other diseases. In some embodiments, the other disease is coronary artery calcification. In further embodiments, the cancer is breast cancer or colorectal cancer. The method includes targeting a G-quadruplex structure in equilibrium with a canonical hairpin structure in the G-rich region of the pre-miRNA-1229 sequence. Targeting the G-quadruplex structure in the rs2291418 SNP located in the pre-miRNA 1229 sequence, which changes the equilibrium between the G-quadruplex structure and the canonical hairpin structure to favor the hairpin structure, controls the production of mature miRNA-1229-3p to correspond with a normal level, and correspondingly upregulating the sortilin-related receptor protein.

For Alzheimer's disease, the method includes stabilizing the equilibrium between the G-quadruplex structure and the canonical hairpin structure to favor the G-quadruplex, lowering the production of mature miRNA-1229-3p to a level corresponding to a normal level, and upregulating the sortilin-related receptor protein to a level corresponding to a normal level.

BRIEF DESCRIPTION OF THE DRAWINGS

FIGS. 1A and 1B, based on RNA structure prediction software, show the most likely hairpin structures for full-length pre-miRNA-1229 WT (SEQ ID NO: 2) and pre-miRNA-1229_SNP (SEQ ID NO: 4), respectively. Pre-miRNA-1229_WT has multiple G-tracts, numbered 1 to 6 in FIG. 1A. G-tracts are also numbered 1 to 6 in FIG. 1B for pre-miRNA-1229_SNP. FIG.

1C shows (nucleotide 6 to 32 of SEQ ID NO: 1) the GQ structure of full-length pre-miRNA-1229 predicted using QGRS Mapper software; in accordance with certain embodiments of the invention.

Figure 2A:
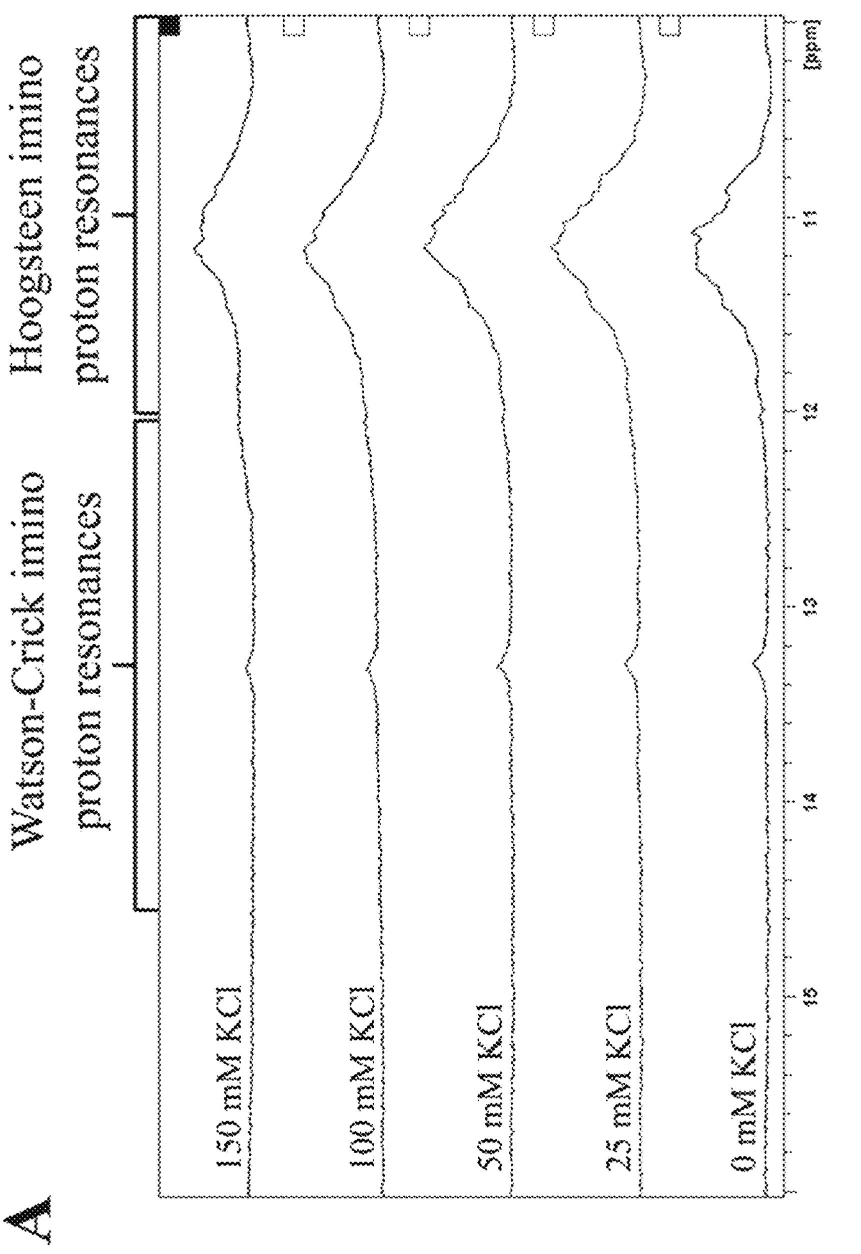
Figure 2B:
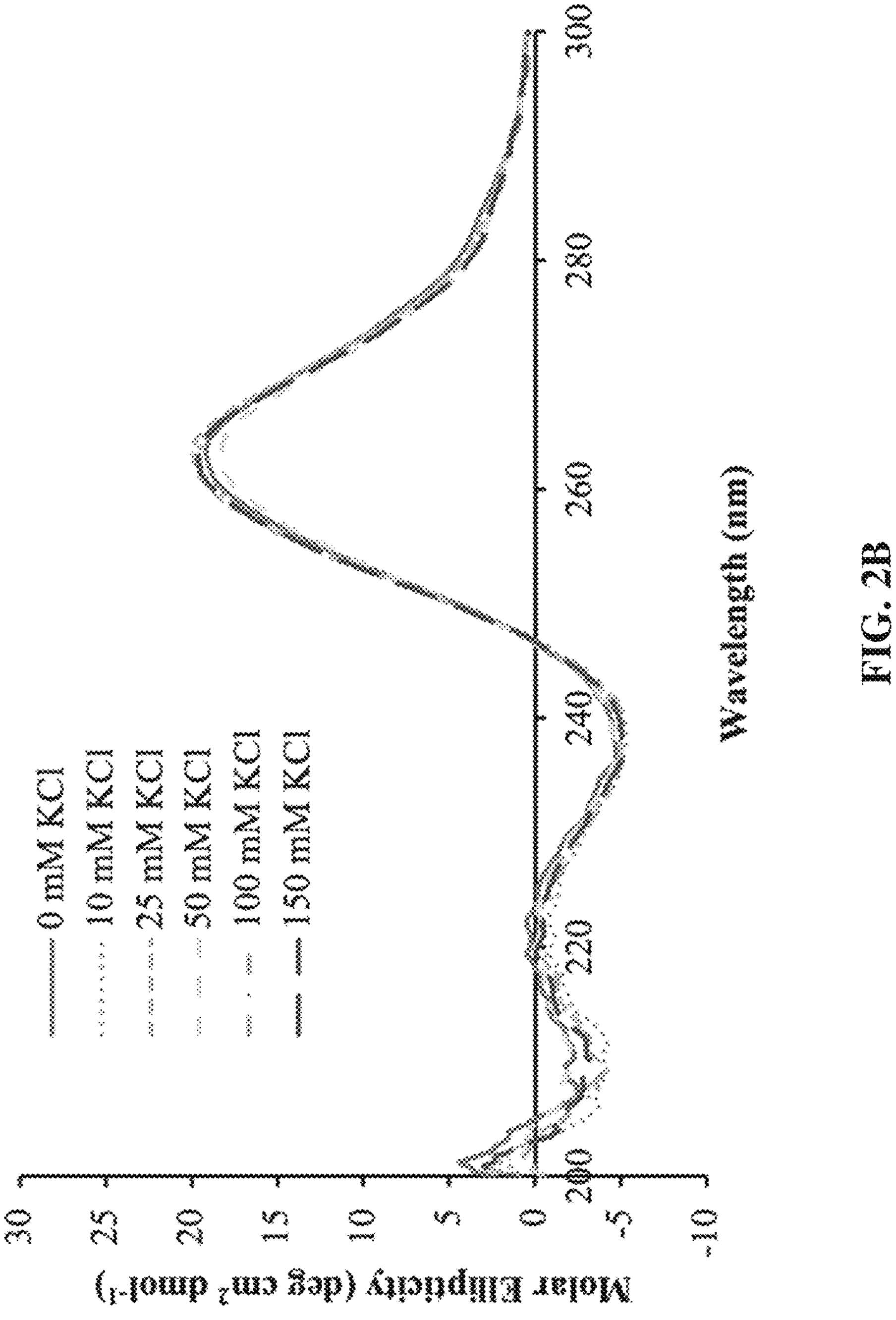

FIGS. 2A and 2B show biophysical characterization of the truncated pre-miRNA-1229_WT GQ sequence for $^1$H NMR spectra and CD spectra, respectively, at various KCl concentrations in 10 mM cacodylic acid, pH 6.5, demonstrating the formation of a GQ structure; FIG. 2C shows the UV thermal denaturation hypochromic transition of 10 μM RNA in 150 mM KCl, to determine a $T_m$ of ~80° C.; FIG. 2D shows the $T_m$ values plotted as a function of the RNA concentration, which shows formation of an intramolecular GQ structure; FIG. 2E shows nondenaturing gel electrophoresis visualized by UV shadow (left panel) and stained with the GQ-specific N-methyl mesoporphyrin IX (NMM) dye (right panel), revealing the formation of a GQ structure at all KCl concentrations; in accordance with certain embodiments of the invention.

Figure 3A:
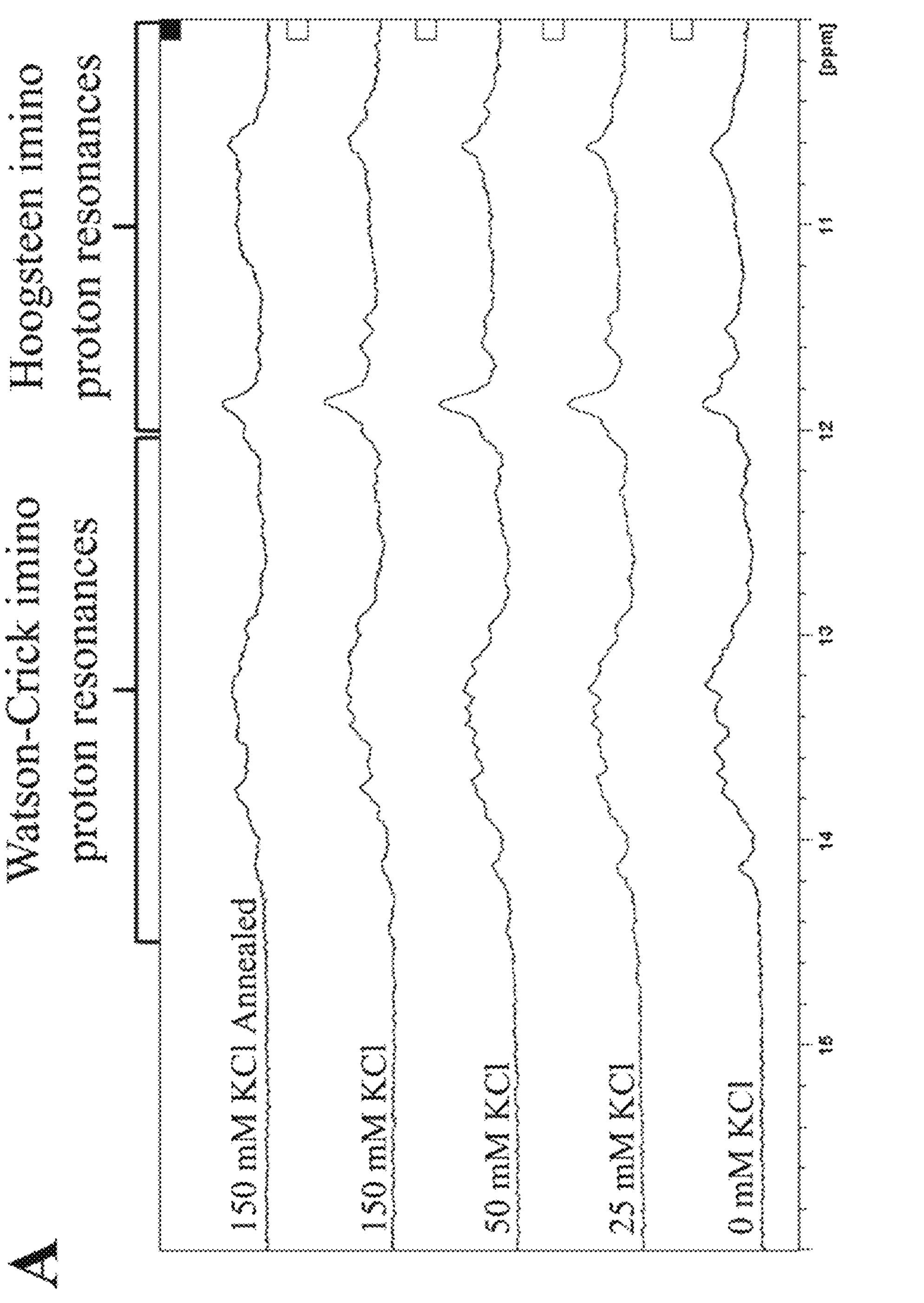
Figure 3B:
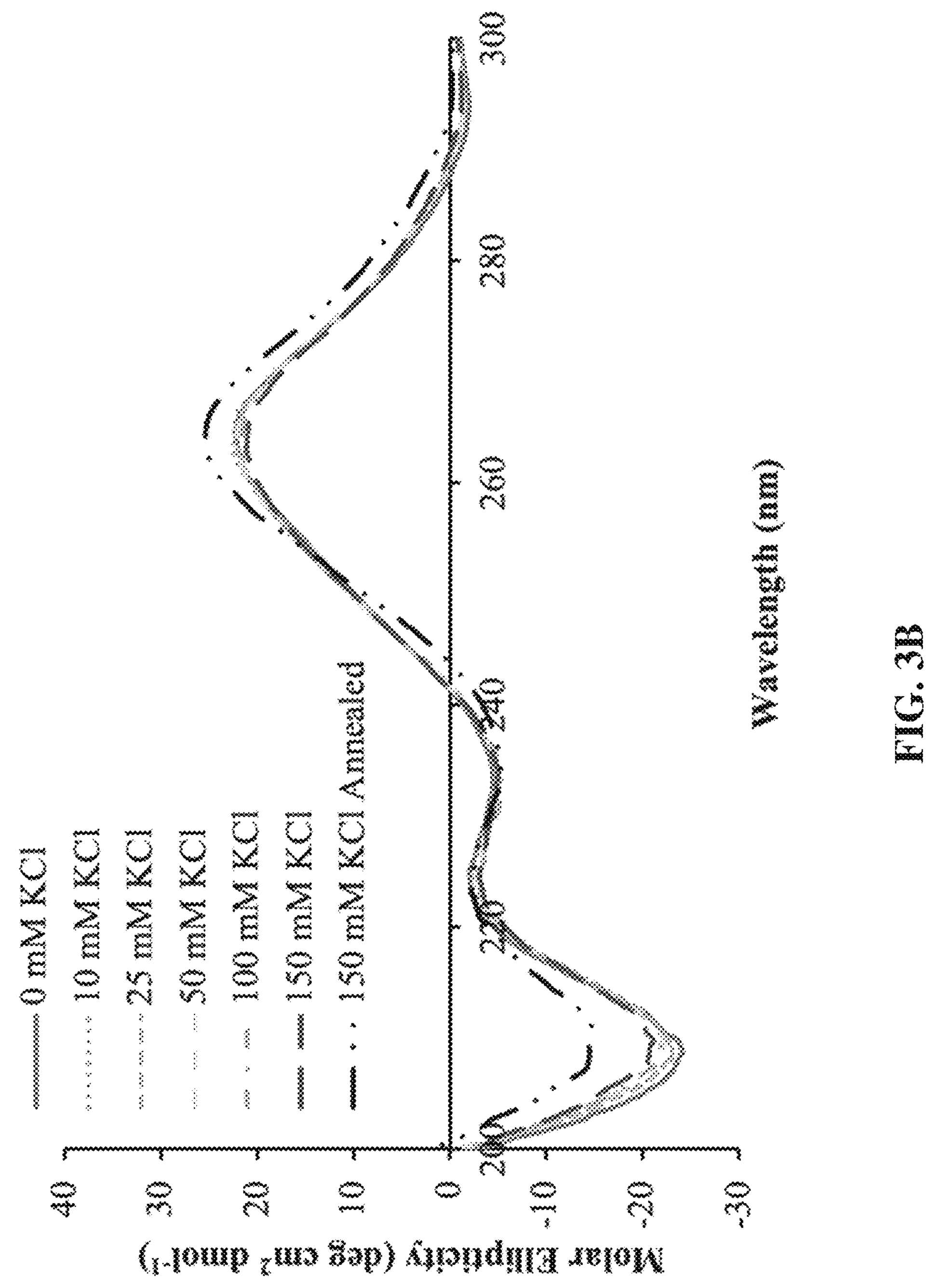
Figures 3C, 3D:
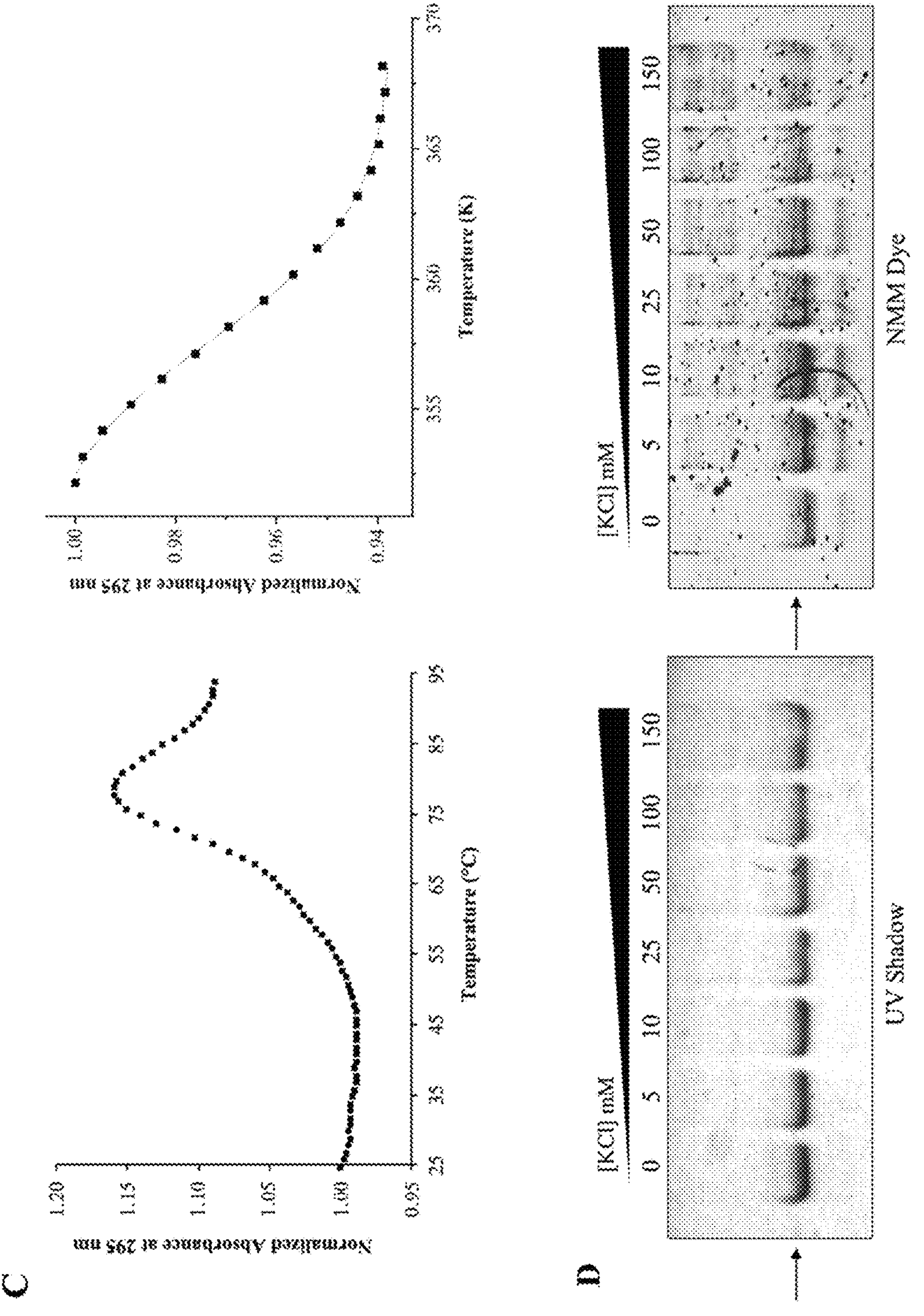

FIGS. 3A-3D show biophysical characterization of the full-length pre-miRNA-1229_WT FL sequence; FIGS. 3A and 3B show $^1$H NMR spectra and CD spectra, respectively, at various KCl concentrations in 10 mM cacodylic acid, pH 6.5, revealing an equilibrium between hairpin and GQ structures after annealing the RNA in 150 mM KCl; FIG. 3C shows UV thermal denaturation hypochromic transition of 10 μM RNA in 100 mM KCl, to determine a $T_m$ of ~85° C.; FIG. 3D shows nondenaturing gel electrophoresis visualized by UV shadow (left panel) and stained with the GQ-specific NMM dye, revealing the formation of multiple GQ structures; in accordance with certain embodiments of the invention.

Figures 4A, 4B:
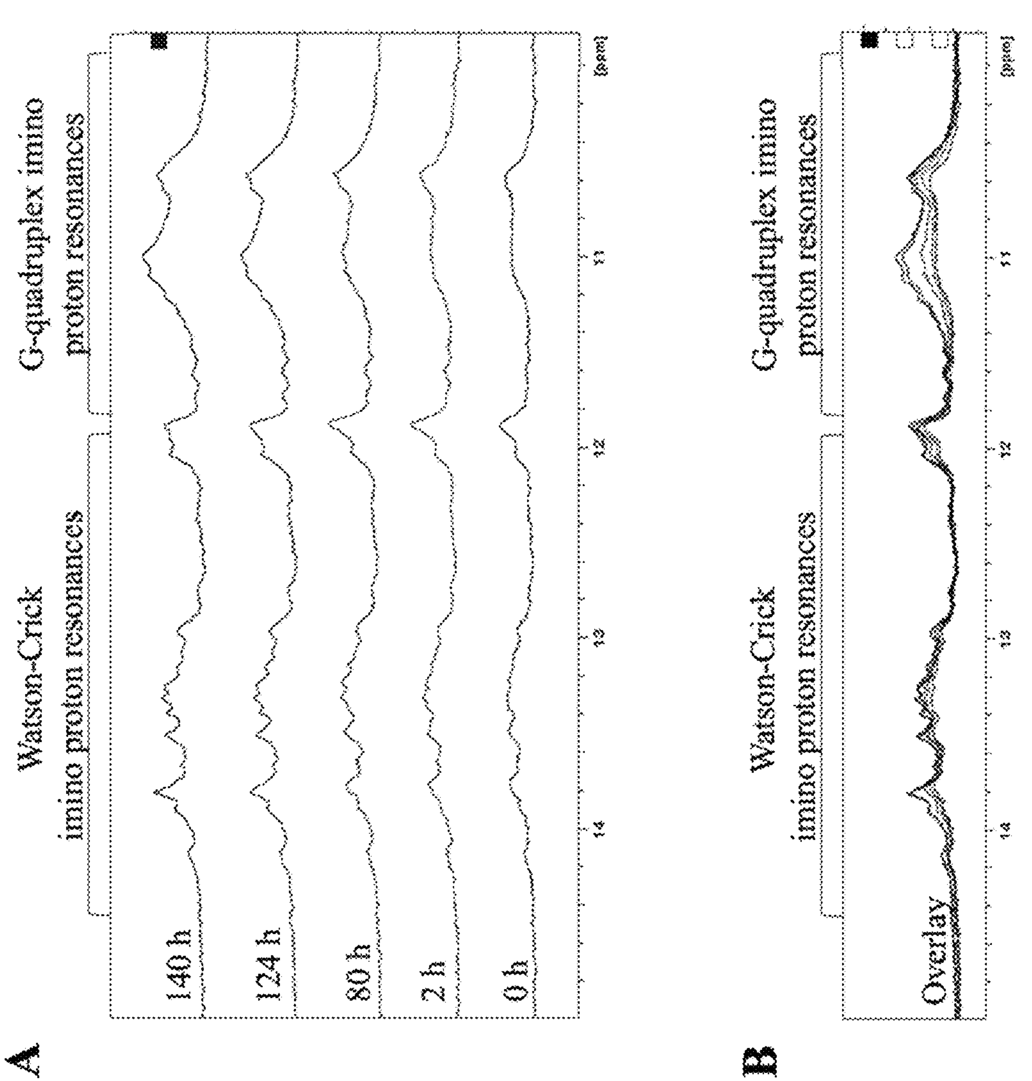

FIG. 4A shows time-dependent $^1$H NMR spectra of full-length pre-miRNA-1229_WT FL in the presence of 150 mM KCl and 1 mM $MgCl_2$; FIG. 4B shows an overlay of the spectra; in accordance with certain embodiments of the invention.

Figure 5A:
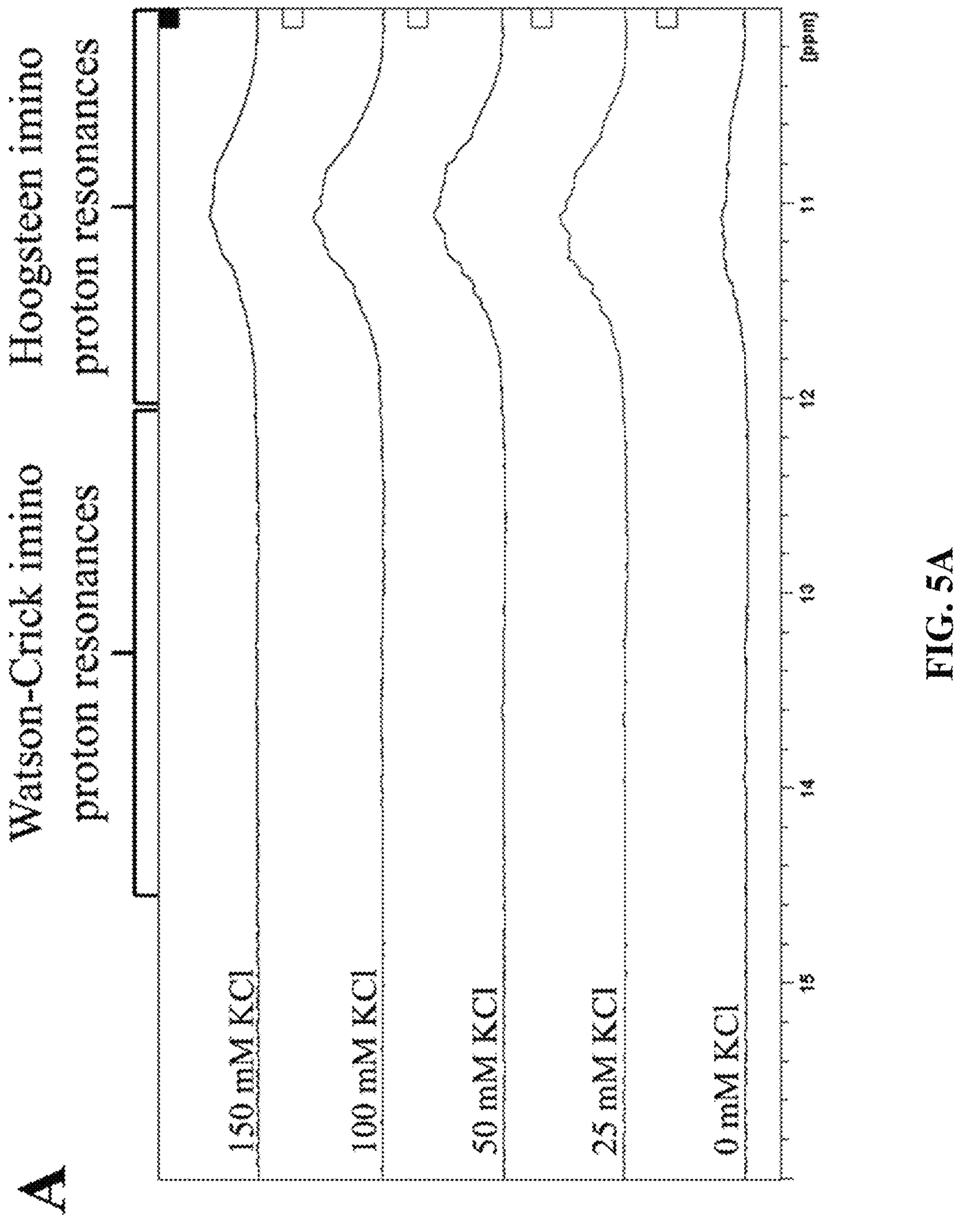
Figure 5B:
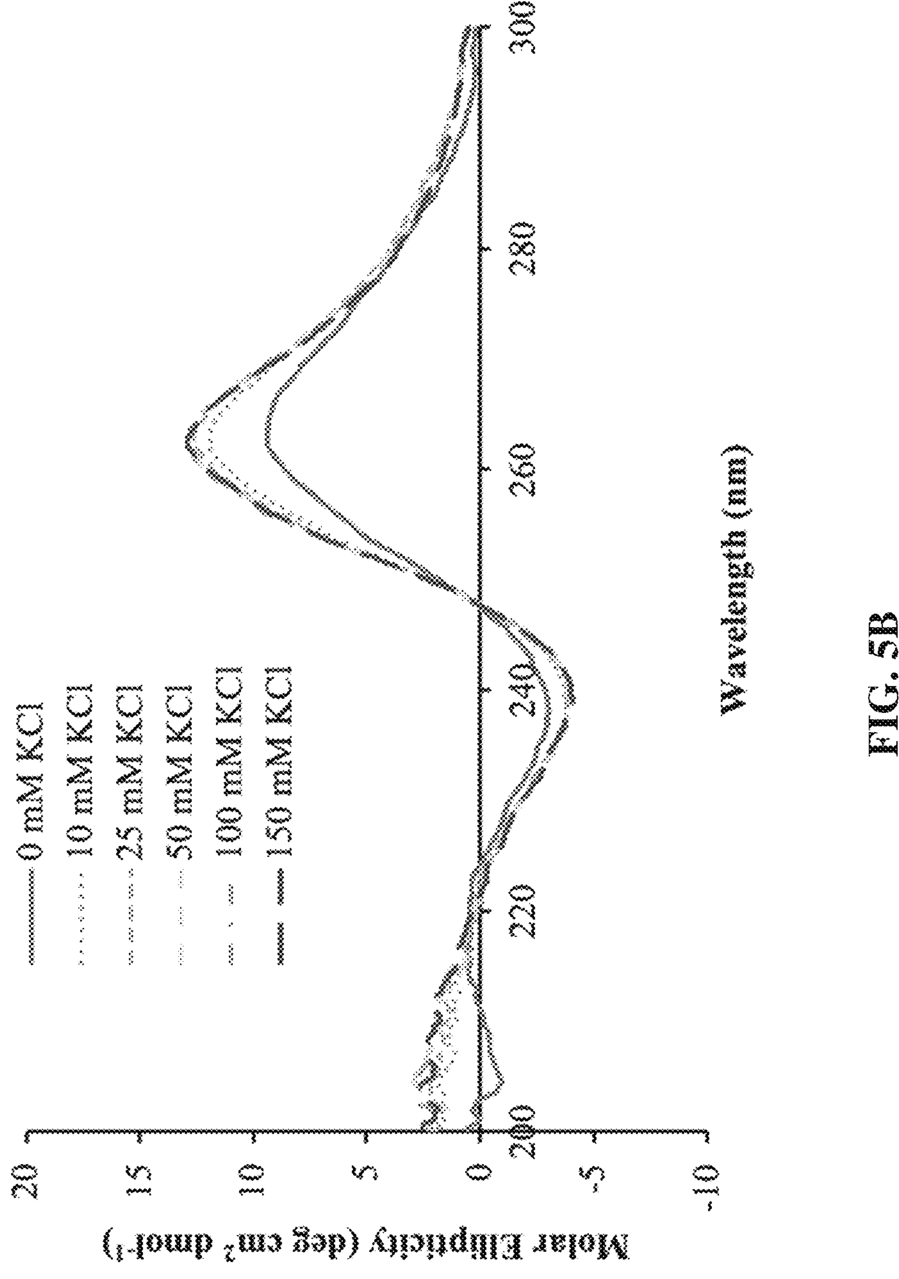

FIGS. 5A and 5B show $^1$H NMR spectra and CD spectra, respectively, at various KCl concentrations in 10 mM cacodylic acid, pH 6.5, demonstrating the formation of a GQ structure; FIG. 5C shows the UV thermal denaturation hypochromic transition of 10 μM RNA in 150 mM KCl, to determine a $T_m$ of ~78° C.; FIG. 5D shows the $T_m$ values plotted as a function of the RNA concentration revealing that an intramolecular GQ structure is formed; FIG. 5E shows nondenaturing gel electrophoresis visualized by UV shadow (left panel) and stained with the GQ-specific NMM dye (right panel), revealing the formation of a GQ structure at all KCl concentrations; in accordance with certain embodiments of the invention.

Figure 6A:
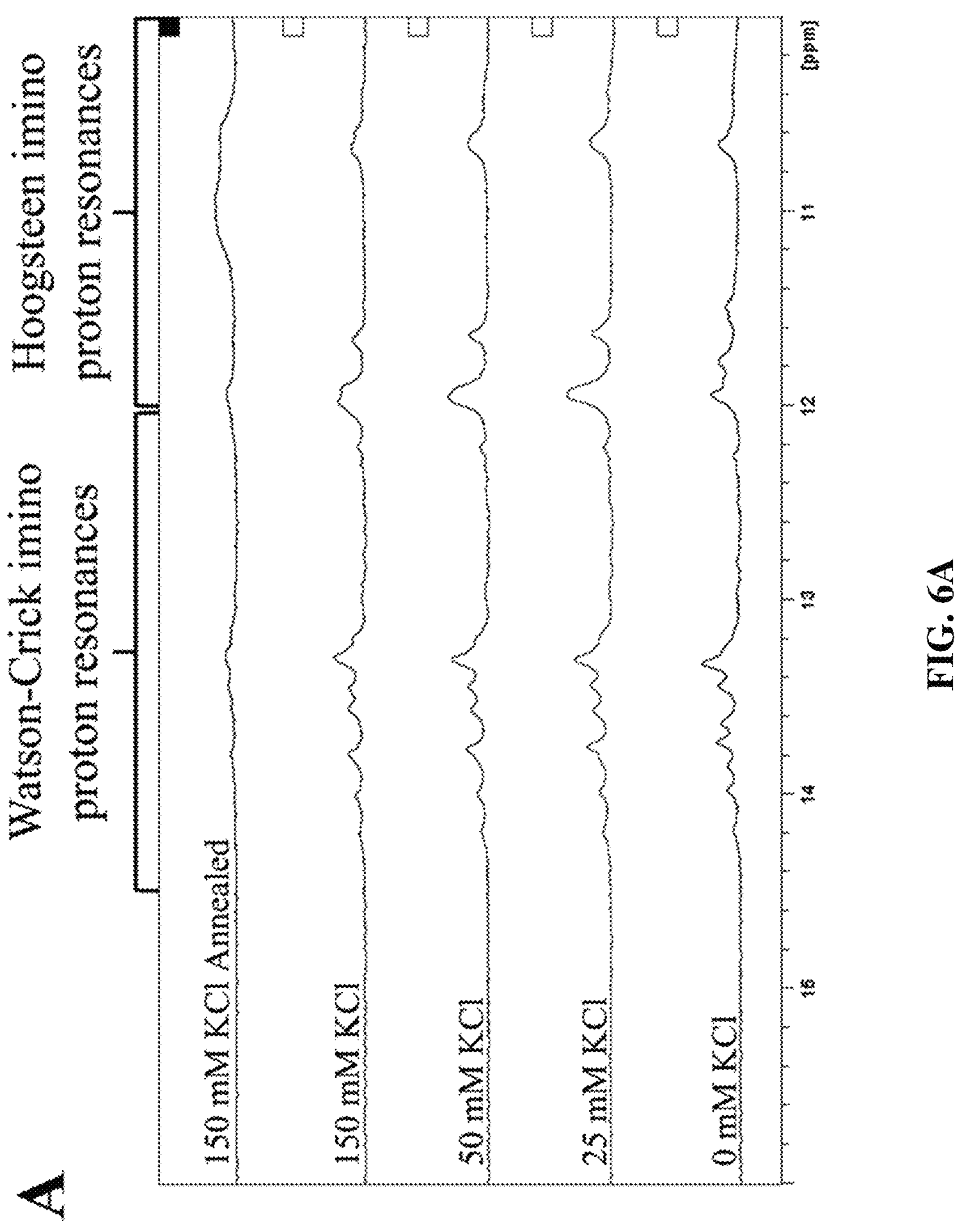
Figure 6B:
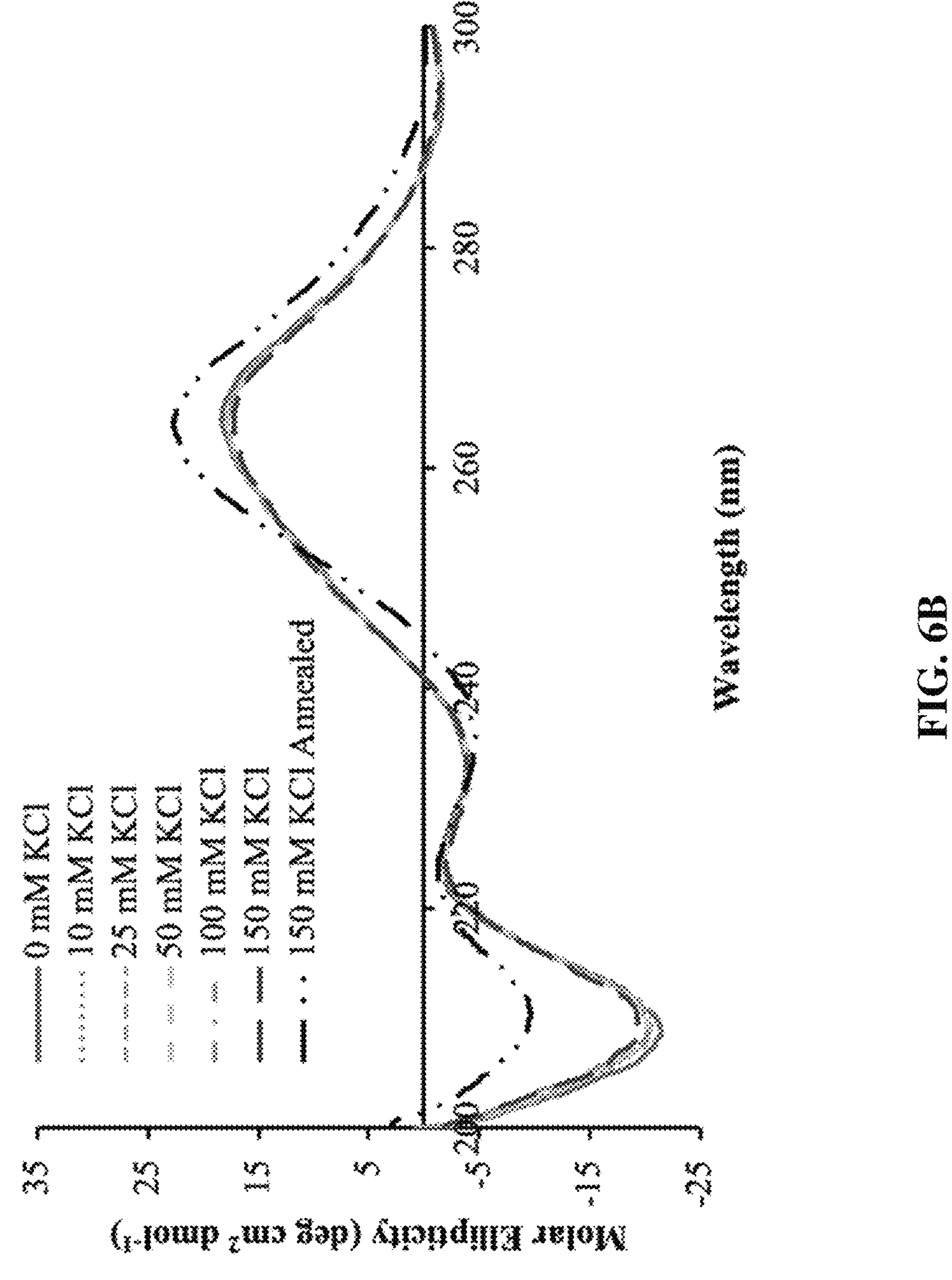
Figures 6C, 6D:
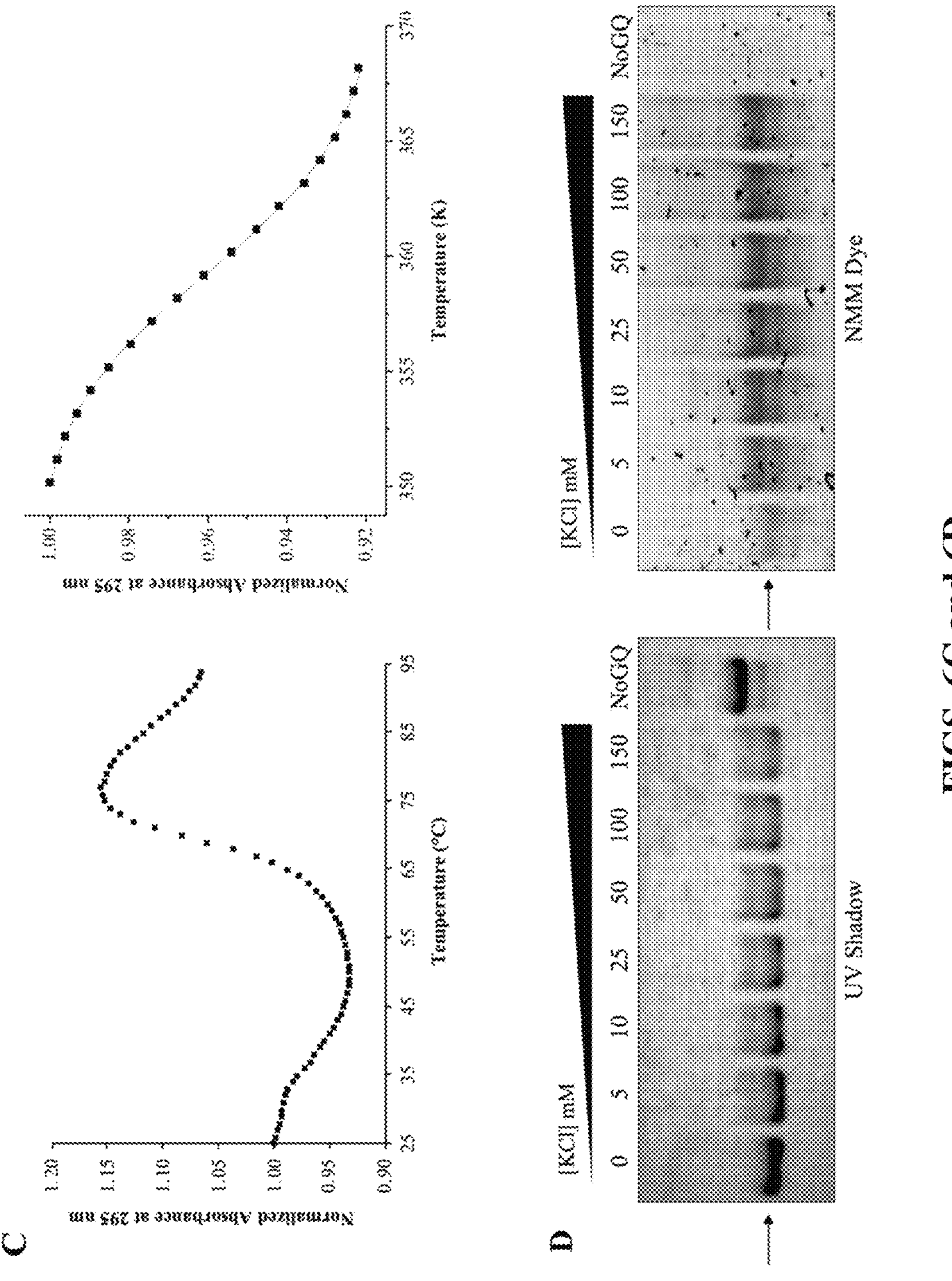

FIGS. 6A and 6B show $^1$H NMR spectra and CD spectra, respectively, at various KCl concentrations in 10 mM cacodylic acid, pH 6.5 reveal an equilibrium between hairpin and GQ structures after annealing the RNA in 150 mM KCl; FIG. 6C shows UV thermal denaturation hypochromic transition of 10 μM RNA in 100 mM KCl, to determine a $T_m$ of ~86° C.; FIG. 6D shows nondenaturing gel electrophoresis visualized by UV shadow (left panel) and stained with the GQ-specific NMM dye (right panel), revealing the formation of multiple GQ structures as well as a hairpin structure; in accordance with certain embodiments of the invention.

Figures 7A, 7B:
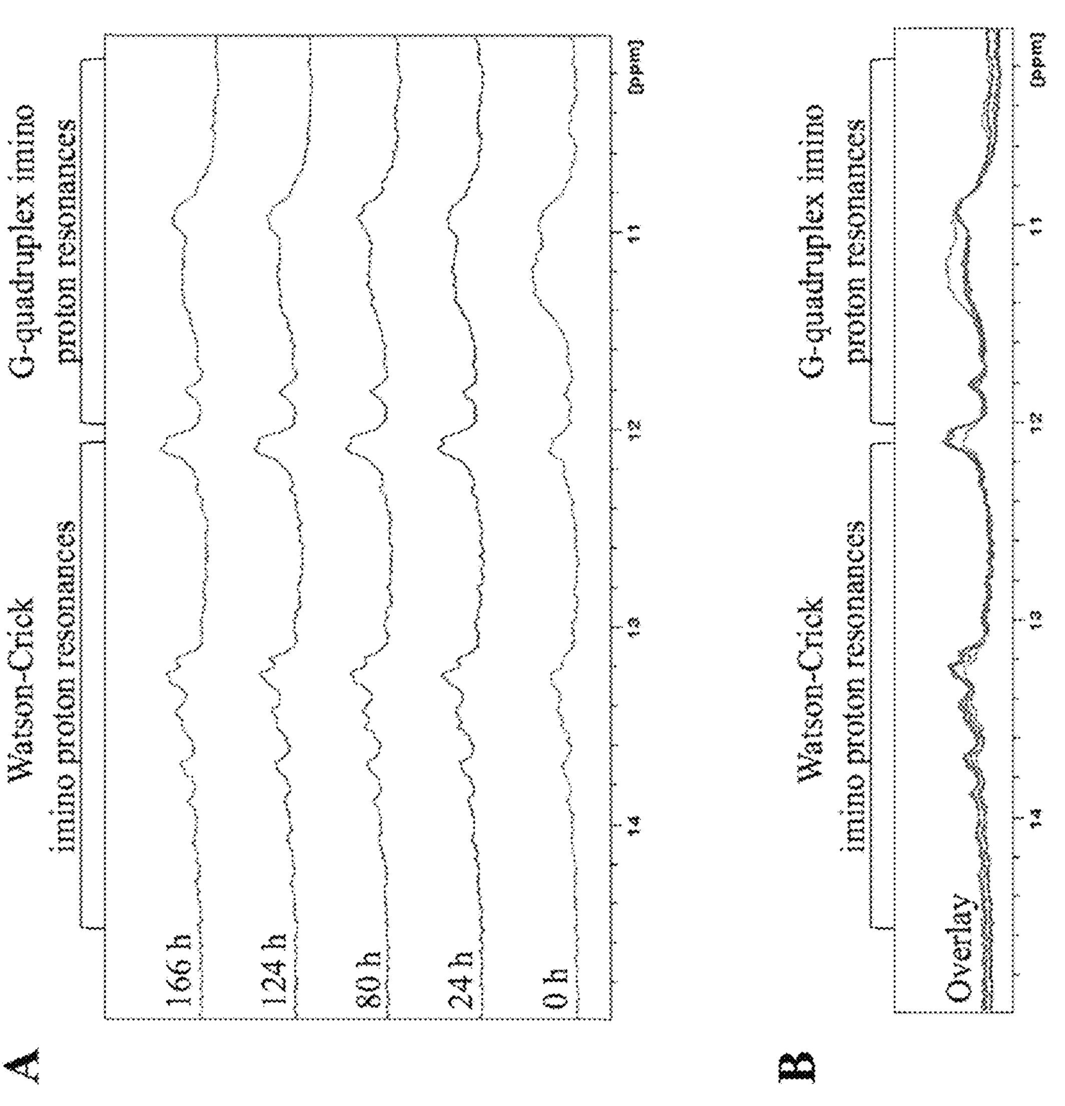

FIG. 7A shows time-dependent NMR spectra of full-length pre-miRNA-1229_SNP FL in the presence of 150 mM KCl and 1 mM $MgCl_2$.

FIG. 7B shows an overlay of the spectra; in accordance with certain embodiments of the invention.

DETAILED DESCRIPTION OF THE PREFERRED EMBODIMENTS

Unless defined otherwise, all technical and scientific terms used herein have the same meaning as is commonly understood by one of skill in the art to which this invention belongs. All publications and patents referred to herein are incorporated by reference.

As used herein, the articles "a" and "an" may refer to one or to more than one (e.g. to at least one) of the grammatical object of the article.

As used herein, "about" may generally refer to an acceptable degree of error for the quantity measured given the nature or precision of the measurements. Example degrees of error are within 5% or 1% of a given value or range of values.

Embodiments described herein as "comprising" one or more features may also be considered as disclosure of the corresponding embodiments "consisting of" and/or "consisting essentially of" such features.

As used herein, a "subject" is an animal which is capable of suffering from or afflicted with a disease. In some embodiments, the subject is a mammal, for example, a human, non-primate, dog, cow, horse, pig, sheep, goat, cat, mouse, rabbit, rat, or transgenic non-human animal.

As used herein, the term "treat" means to relieve, reduce or alleviate at least once symptom of a disease in a subject.

As used herein, a "therapeutically effective amount" of a therapeutic agent, or combinations thereof, is an amount sufficient to treat disease in a subject. For example, for an agent for treating Alzheimer's disease, a therapeutically effective amount can be an amount that has been shown to provide an observable therapeutic benefit compared to baseline clinically observable signs and symptoms of Alzheimer's disease.

As used herein, the term "PNA" means a peptide nucleic acid. PNAs are nucleic acid analogs in which the sugar phosphate backbone of natural nucleic acid has been replaced by a synthetic peptide backbone. In some embodiments, gamma PNAs are employed. PNAs and gamma PNAs are described in Oyaghire, S. N. et al. (2016) *Biochemistry,* 55, 1977-1988, which is hereby incorporated by reference in its entirety. In some embodiments, the PNA or gamma PNA further comprises a C-terminal lysine residue.

Concentrations, amounts, volumes, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

Provided is a G-quadruplex (GQ) structure within pre-miRNA-1229 as a novel therapeutic target in Alzheimer's disease (AD), various cancers, and other diseases, and for methods of treating AD, various cancers, and other diseases, as well as methods of mitigating the progression or precluding the onset of AD, various cancers, and other diseases.

Among the pre-miRNAs with G-rich sequences that have the potential to form GQ structures is pre-miRNA-1229, whose mature miRNA product, miRNA-1229-3p, has been shown to directly control the expression of SORL1. Moreover, the allelic guanine to adenine rs2291418 variant (cytosine to uracil in the RNA) within pre-miRNA-1229 is associated with AD and this single nucleotide polymorphism (SNP) enhances the production of miRNA-1229-3p and decreases the levels of SORL1, as further detailed below.

Gene expression is regulated by miRNAs that repress the translation of specific messenger RNA targets. In various diseases, dysregulation in the biogenesis of precursor miRNAs (pre-miRNA) results in either an upregulation or a downregulation of mature miRNAs. Approximately 13-16% of human pre-miRNA sequences contain guanine-rich (G-rich) regions that have the potential to form GQ structures. GQs are non-canonical secondary structures formed by stacking of two or more cyclic, planar G-quartet arrangement of four guanine residues and stabilized by Hoogsteen-type hydrogen bonds, 11-71 stacking interactions, and intercalating monovalent cations.

The inventors have found that a GQ structure exists in the G-rich region of pre-miRNA-1229 that could alter the efficiency of mature miRNA production. Pre-miRNA-1229 is the immediate precursor in the formation of mature miRNA-1229-3p. As a result of a single nucleotide polymorphism (SNP) correlated with AD, the level of mature miRNA-1229-3p is increased as compared to corresponding normal levels in subjects that do not have this SNP.

Furthermore, it has been shown that the GQ structure co-exists in equilibrium with a canonical hairpin structure. The mutation in the AD-associated rs2291418 pre-miRNA-1229 SNP shifts the equilibrium towards the hairpin structure. As a result, it has been proposed that the rs2291418 variant enhances the production of miRNA-1229-3p and decreases levels of sortilin-related receptor (SORL1). The downregulated expression of SORL1 results in APP being sorted into Aβ-generating pathways.

Since only the hairpin structure of pre-miRNA-1229 is processed into the mature miRNA-1229-3p, the presence of the GQ structure serves as a fine-tuning mechanism that controls the production of mature miRNA-1229-3p and ultimately, regulation of SORL1 protein. Thus, for AD, the GQ should be stabilized to decrease the production of mature miRNA-1229-3p to a level observed in normal subjects that do not have AD and ultimately, to upregulate the SORL1 protein. In certain other diseases, the GQ should be destabilized to increase the production of mature miRNA-1229-3p to a level observed in normal subjects that do not have the disease and ultimately, SORL1 protein is downregulated.

Thus, in accordance with the invention, formation of GQ structures and control of the equilibrium between the GQ and hairpin structures are effective to control the levels of mature miRNA-1229 that, in turn, regulates SORL1 translation to decrease or preclude APP being sorted into Aβ-generating pathways, thereby impacting AD. The mature miRNA-1229-3p exerts a fine-tuning regulation in the translation of SORL1 in normal subjects, whereas its overproduction observed in AD due to the SNP rs2291418 in pre-miRNA-1229 results in a downregulation of the SORL1 production that in turn affects the clearance of the Aβ complex. Additionally, since expression levels of miRNA-1229 are correlated with increased severity of coronary artery calcification and increased tumor size in colorectal and breast cancer, this mechanism for AD is also applicable to various cancers and other diseases. In other diseases, such as but not limited to, amyotrophic lateral sclerosis, autism, and Down syndrome, dysregulation in biogenesis of pre-miRNAs results in either an upregulation or a down regulation of mature miRNAs. Thus, stabilization or destabilization of the GQ in the pre-miRNA-1229 would either decrease or increase, respectively, the production of the mature miRNA-1229 to levels observed in normal subjects that do not have the disease.

The GQ structure is provided as a therapeutic target, whereby targeting the GQ structure reduces the level of mature miRNA-1229 and restores the level of SORL1 protein to those observed in normal subjects. This approach is more advantageous than targeting AR depletion, because it does not preclude AR from exerting its beneficial functions.

Provided is an agent that binds to a wild type or variant pre-miRNA-1229 comprising a G-quadruplex (GQ) structure, wherein binding of the agent to the wild type or variant pre-miRNA-1229 stabilizes the GQ structure of the wild type or variant pre-miRNA-1229. In some embodiments, the variant is rs2291418. This will result in producing less of the mature miRNA-1229, since when folded in the GQ structure, pre-miRNA-1229 cannot be processed by Dicer.

In some embodiments, the agent comprises an engineered protein nucleic acid (PNA). In further embodiments, the PNA is a gamma PNA.

In some embodiments, the PNA or gamma PNA is selected from the group consisting of:

```
                              (SEQ ID NO: 5)
AGCCCACGCUCUCCCCCAAA

                              (SEQ ID NO: 6)
UGAACCCCAGCCCACGCUCU;
and

                              (SEQ ID NO: 7)
GGGUGUCCCUGAACCCCAGC.
```

In some embodiments, the PNA or gamma PNA comprises a C-terminal lysine residue, and is selected from the group consisting of (the bolded C repeats target the G repeats forming the GQ):

(SEQ ID NO: 5)
$H_2$N-Lys AGCCCACGCUCUCCCCCAAA-H (SEQ ID NO: 6)
$H_2$N-Lys UGAACCCCAGCCCACGCUCU-H;
and (SEQ ID NO: 7)
$H_2$N-Lys GGGUGUCCCUGAACCCCAGC-H.

In some embodiments the agent comprises 2'-deoxy 2'-fluoroarabino (2'-FANA) oligonucleotides. In further embodiments the 2'-FANA oligonucleotides comprise a sequence selected from the group consisting of:

```
                              (SEQ ID NO: 8)
AGCCCACGCUCUCCCCCAAA

                              (SEQ ID NO: 9)
UGAACCCCAGCCCACGCUCU;
and

                             (SEQ ID NO: 10)
GGGUGUCCCUGAACCCCAGC.
```

FANA oligonucleotides have the ability to penetrate the cell membrane by gymnosis, which is the process by which antisense oligodeoxynucleotides are delivered to cells, in the absence of any carriers or conjugation (Souleimanian, N. et al. (2012) *Mol. Ther.—Nucleic Acids,* 1, e43).

In some embodiments, the agent comprises a small molecule. Small molecules that stabilize the GQ structure of the wild type or variant pre-miRNA-1229 may be identified through using a small molecule microarray (SMM) high throughput screening platform.

Provided is a method of treating a disease in a subject, comprising: administering a therapeutically effective amount of the agent of any one of the previous embodiments to the subject. In some embodiments, the disease is Alzheimer's disease, cancer or coronary artery calcification. In further embodiments, the cancer is breast cancer or colorectal cancer.

Also provided is a composition comprising the agent of any one of the embodiments described herein.

Provided is a method of treating a disease in a subject, comprising: administering a therapeutically effective amount of the composition comprising the agent of any one of the embodiments described herein to the subject. In some embodiments, the disease is Alzheimer's disease, cancer or coronary artery calcification. In further embodiments, the cancer is breast cancer or colorectal cancer.

EXAMPLES

In these experiments, various biophysical techniques were used to show that a GQ structure forms in pre-miRNA-1229 which coexists in equilibrium with a canonical extended hairpin structure, and that this equilibrium is shifted in the rs2291418 variant towards the hairpin structure. The results indicate a mechanism leading to increased production of the mature miRNA-1229-3p in AD with the correlated rs2291418 SNP in pre-miRNA-1229 and suggest using the GQ structure within pre-miRNA-1229 as a therapeutic target in these cases.

Materials and Methods

In Vitro RNA Synthesis

Pre-miRNA sequences (Table 1) were produced by in vitro transcription reactions using T7 RNA polymerase (synthesized in-house), following aprocedure by Milligan and Uhlenbeck. The DNA templates for each sequence were chemically synthesized by TriLink Biotechnologies, Inc. (San Diego, CA, USA). The RNA oligonucleotides were purified by 20%-8 M urea denaturing polyacrylamide gel electrophoresis (PAGE) and electrophoretic elution, followed by extensive dialysis against 10 mM cacodylic acid, pH 6.5. The concentration of each oligonucleotide was measured using a NanoDrop 2000 UV-Vis spectrophotometer (ThermoFisher Scientific, Waltham, MA, USA), and their purity was checked by denaturing gel electrophoresis.

$^{1}$H NMR Spectroscopy

One-dimensional (1D) proton ($^{1}$H) NMR spectroscopy experiments were performed on a 500 MHz Bruker AVANCE spectrometer (Bruker Corporation, Billerica, MA, USA) at 25° C. using Topspin 3.2 software. Water suppression was carried out by using the Watergate pulse sequence. Pre-miRNA samples with concentrations ranging from 100 to 300 μM were prepared in a volume of 250 μL 10 mM cacodylic acid, pH 6.5, in a 90:10 ratio of $H_2O$:$D_2O$. GQ formation was observed by titrating increasing concentrations of KCl from a 2 M stock solution to each sample. The samples containing 150 mM KCl were also annealed by boiling at 95° C. for 5 minutes and cooling on the bench for 15 minutes. Time-dependent NMR spectroscopy studies were conducted following the addition of 1 mM $MgCl_2$ to each sample and incubating at 37° C. while acquiring spectra overtime.

Circular Dichroism Spectroscopy

Circular dichroism (CD) spectroscopy experiments were recorded on a Jasco J-810 spectropolarimeter (JASCO, Easton, MD, USA) at 25° C. Pre-miRNA samples were prepared in 10 mM cacodylic acid, pH 6.5 to a final RNA concentration of 10 μM in a volume of 200 μL. GQ formation was monitored by titrating increasing amounts of KCl from a 2 M stock solution to each sample and subsequently annealing the sample at 95° C. for 5 minutes once a final KCl concentration of 150 mM was reached. Spectra were measured between 200 and 300 nm and corrected for solvent contributions. Each spectrum was scanned seven times with a 1 second response time and a 2 nm bandwidth. CD spectroscopy experiments were performed in duplicate (n=2) for each RNA.

UV Spectroscopy Thermal Denaturation

Thermal denaturation experiments were conducted using a Varian Cary 3E UV/Vis spectrophotometer (Agilent, Santa Clara, CA, USA) equipped with a Peltier cell. RNA samples were annealed in 10 mM cacodylic acid, pH 6.5, containing 100-150 mM KCl. Samples were heated from 25 to 95° C. at a rate of 0.2° C. $min^{-1}$, recording points every 1° C. at 295 nm, a wavelength previously identified to be sensitive to G-quadruplex dissociation. To determine if the structures folded into intermolecular or intramolecular conformations, the melting temperatures of the G-quadruplex structures were determined at various RNA concentrations. The transitions of each dissociation were identified and fitted with Equation (1):

$$A(T) = \frac{A_{\mu} + A_F e^{-\Delta H^{\circ}/RT} e^{\Delta S^{\circ}/R}}{e^{-\Delta H^{\circ}/RT} e^{\Delta S^{\circ}/R} + 1} \quad (1)$$

where $A_U$ and $A_F$ represent the absorbance of the unfolded and native GQ RNA, respectively, and R is the universal gas constant.

Nondenaturing Polyacrylamide Gel Electrophoresis

RNA samples were prepared with varying KCl concentrations and a constant RNA concentration of 10 μM, followed by heating for 5 minutes at 95° C. and slow cooling to room temperature. Samples were run on 15% or 20% acrylamide gels and visualized using an Alphalmager (ProteinSimple, San Jose, CA, USA) by UV shadowing at 254 nm. Gels were subsequently stained in N-methyl mesoporphyrin IX (NMM), a GQ-specific fluorescent probe, and visualized to determine if the GQ structure formed at various concentrations of KCl. Gel electrophoresis experiments were performed in triplicate (n=3) for each RNA.

Example 1: The G-Rich Region of Pre-miRNA-1229 Folds into a GO Structure

Figures 1A, 1B:
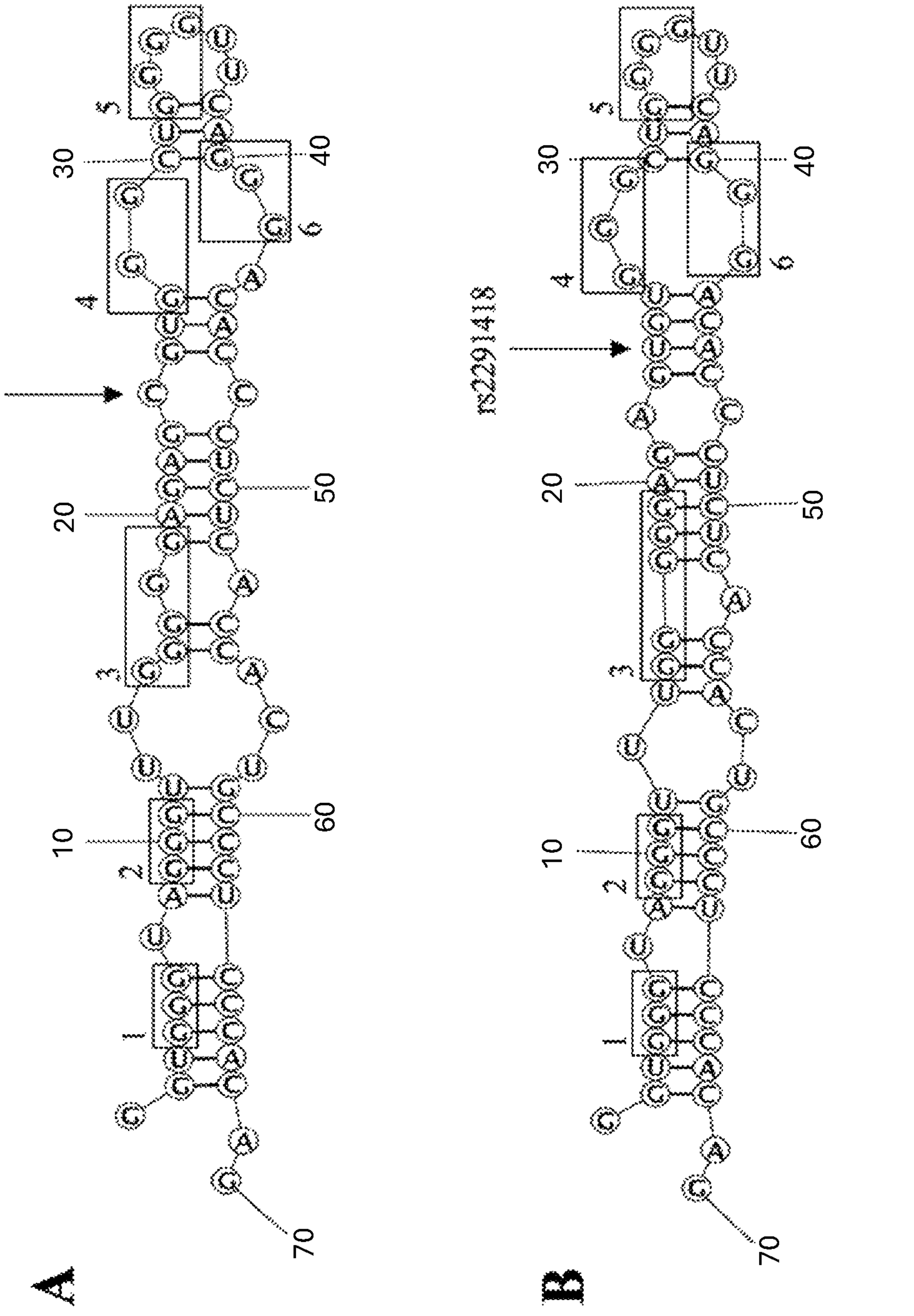
FIGS. 1A, 1B and 1C show predicted secondary structures of pre-miRNA-1229 sequences.
Figure 1C:
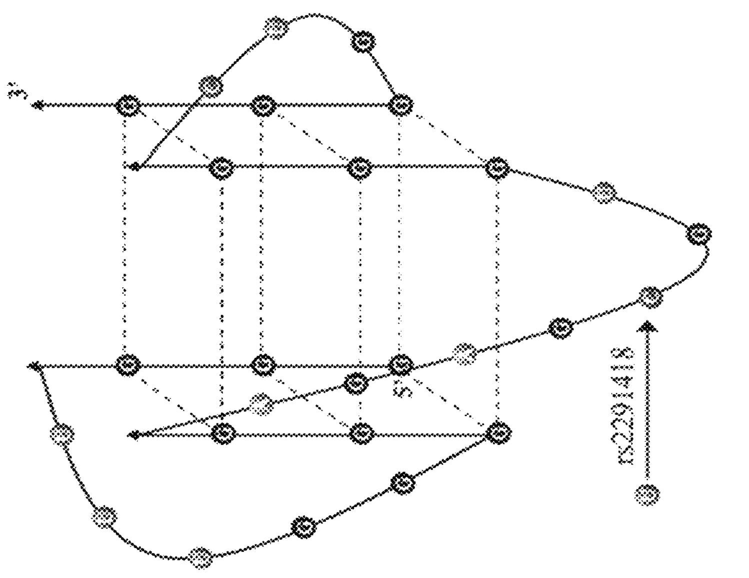

The formation of GQ structures in pre-miRNA sequences was proposed to alter the efficiency of miRNA production. Since pre-miRNA-1229 has multiple G-tracts, numbered 1 to 6 in FIG. 1A, the online QGRS Mapper (bioinformatics.ramapo.edu/QGRS/analyze.php) software was used, which predicted that a three-plane GQ structure can form in this pre-miRNA using the G-tracts 2, 3, 4, and 5 (FIGS. 1A,C). A truncated sequence spanning nucleotides 1-42 of pre-miRNA-1229 that contains the six G-tracts that could participate in GQ structure formation (named pre-miRNA- 1229_WT GQ, Table 1), was investigated to determine if this G-rich region of pre-miRNA-1229 indeed folds into the predicted GQ structure. With respect to FIGS. 1A and 1B, RNAStructure prediction software (ma.urmc.rochester.edu/RNAstructureWeb/) was used to determine the most likely hairpin structures for full-length pre-miRNA-1229 WT (FIG. 1A) and pre-miRNA-1229_SNP (FIG. 1B). G-tracts are numbered and highlighted by shaded boxes. The location of the SNP is indicated with an arrow in both structures. The predicted GQ structure of full-length pre-miRNA-1229 was determined using the online QGRS Mapper software (FIG. 1C). Nucleotides involved in GQ formation are shown and the location of SNP is indicated with an arrow.

TABLE 1

RNA sequences used in this study. G-rich areas within pre-miRNA sequences with potential to form G-quadruplex structures are underlined. The SNP mutation locations are highlighted in bold and italic.

| SEQ ID NO | Name | Sequence |
|---|---|---|
| 1 | pre-miRNA-1229_WT GQ | 5' GGGUAGGGUUUGGGGGAGAG***C***GUGGGCUGGGGUUCAGGG ACA-3' |
| 2 | pre-miRNA-1229_WTFL | 5' GGUGGGUAGGGUUUGGGGGAGAG***C***GUGGGCUGGGG UUCAGGGACACCCUCUCACCACUGCCCUCCCACAG 3' |
| 3 | pre-miRNA-1229_SNP GQ | 5' GGGUAGGGUUUGGGGGAGAG***U***GUGGGCUGGGGUUCAGGG ACA-3' |
| 4 | pre-miRNA-1229_SNP FL | 5' GGUGGGUAGGGUUUGGGGGAGAG***U***GUGGGCUGGGG UUCAGGGACACCCUCUCACCACUGCCCUCCCACAG 3' |

The pre-miRNA-1229_WT GQ RNA was characterized using 1D $^1$H NMR spectroscopy focusing on the imino proton resonance region between 10 and 15 ppm and titrating increasing KCl concentrations in the range of 0-150 mM, as $K^+$ ions stabilize GQ structures (FIG. 2A). Broad resonances were apparent even at 0 mM KCl in the 10-12 ppm region corresponding to guanine imino protons involved in Hoogsteen base pairs in GQ structures. Another resonance was also evident around 13.3 ppm, within the imino proton region 12-14.5 ppm assigned to imino protons involved in Watson-Crick base pairs (FIG. 2A, bottom spectrum). It was hypothesized that this resonance has arisen from Watson-Crick loop-loop interactions within the GQ structure. Increasing KCl concentrations did not seem to have an effect on the intensity of the resonances in the GQ region (FIG. 2A), indicating that a GQ structure was stably formed even in the absence of $K^+$. RNA sequences have been shown to form stable GQ structures even in the absence of $K^+$ ions, while these ions are required for GQ formation in DNA of identical sequence. FIGS. 2A and 2B show biophysical characterization of the truncated pre-miRNA-1229_WT GQ sequence for $^1$H NMR spectra and CD spectra, respectively, at various KCl concentrations in 10 mM cacodylic acid, pH 6.5, demonstrating the formation of a GQ structure. FIG. 2C showing the UV thermal denaturation hypochromic transition at 10 μM RNA in 150 mM KCl was fit using Equation (1) (Materials and Methods), to determine a $T_m$ of ~80° C. FIG. 2D shows the $T_m$ values plotted as a function of the RNA concentration revealed that an intramolecular GQ structure is formed. FIG. 2E shows nondenaturing gel electrophoresis visualized by UV shadow (left panel) and stained with the GQ-specific N-methyl mesoporphyrin IX (NMM) dye (right panel), revealing the formation of a GQ structure at all KCl concentrations.

While both parallel and anti-parallel GQ structures have been observed in DNA, RNA GQs typically only adopt a parallel directionality. To determine the directionality of the GQ structure in pre-miRNA-1229 WT GQ, circular dichroism (CD) spectroscopy experiments were performed. Parallel GQ structures showed a positive band at ~265 nm and a negative band at ~240 nm, whereas the signatures of an antiparallel GQ were a positive band at ~295 nm and a negative band at ~260 nm. The experiments confirmed that a parallel GQ forms within pre-miRNA-1229_WT GQ, as there was observed a positive band at ~265 nm and a negative one at ~240 nm. Moreover, the intensity of these bands changed minimally as the KCl concentration was increased (FIG. 2B), consistent with the $^1$H NMR spectroscopy results (FIG. 2A), indicating that the GQ structure formed by pre-miRNA-1229_WT GQ was stable even in the absence of $K^+$ ions. Helical structures in A-RNA gave rise to a positive band at 260 nm, a negative band at 210 nm, and a small negative CD between 290 and 300 nm. A low intensity negative band at ~210 nm was observed, however, since the intensity of this band was too low with respect to that of the positive band at 260 nm and a small negative CD between 290 and 300 nm was not observed, the formation of a hairpin structure in pre-miRNA-1229_WT GQ was ruled out. Similar to the $^1$H NMR spectroscopy single resonance at 13.3 ppm, the origin of the 210 nm small intensity band was assigned to Watson-Crick loop-loop interactions within the GQ structure.

To determine the overall stability of the GQ structure formed in pre-miRNA-1229_WT GQ, UV thermal denaturation experiments at 295 nm, wavelength sensitive to GQ structure dissociation, at a fixed KCl concentration of 150 mM and a range of RNA concentrations from 5 to 50 μM were performed. At all RNA concentrations investigated, a single hypochromic transition corresponding to the unfolding of a GQ structure was observed. The melting temperature ($T_m$) of the GQ structure at each RNA concentration was determined by fitting this hypochromic transition with Equation (1) (Materials and Methods) (FIG. 2C) to be –80° C. at all RNA concentrations investigated (FIG. 2D), indicating that pre-miRNA-1229_WT GQ formed an intramolecular GQ structure.

The pre-miRNA-1229_WT GQ was then analyzed by 20% nondenaturing polyacrylamide gel electrophoresis at various KCl concentrations in the range of 0-150 mM (FIG. 2E). A main band was observed at each KCl concentration when the gel was visualized by UV shadowing (FIG. 2E, left panel). This band stained in N-methyl mesoporphyrin IX(NMM), a GQ-specific dye (FIG. 2E, right panel), revealing that it corresponds to a GQ structure. Additionally, a lower band became clearly visible in the NMM stained gel, indicating the formation of an alternate GQ structure. While FIG. 1C depicts the most stable GQ structure predicted by the QGRS Mapper software, multiple GQ structures could be formed in pre-miRNA-1229_WT GQ because it contains six G-tracts and only four of these are required for the formation of a GQ structure. A negative control RNA that cannot form a GQ structure (NoGQ) was visible when the gel was visualized by UV shadowing (FIG. 2E, left panel), but absent when stained with NMM (FIG. 2E, right panel). Taken together, the results from these biophysical studies confirm the formation of a parallel, intramolecular GQ structure with a $T_m$ of ~80° C. in 150 mM KCl in the truncated pre-miRNA-1229_WT GQ sequence.

Example 2: Full-Length Pre-miRNA-1229 Forms a GQ Structure That Coexists in Equilibrium with an Extended Hairpin Structure These experiments investigated if the GQ structure formed by the G-rich region of pre-miRNA-1229 is retained within the full-length pre-miRNA-1229_WT sequence (pre-miRNA-1229_WT FL, Table 1), where additional nucleotides past position 42 compete for the formation of the canonical extended hairpin structure. 1D $^{1}$H NMR spectroscopy experiments were performed to monitor secondary structure formation by observing the imino proton resonance region while titrating increasing KCl concentrations (FIG. 3A). Multiple resonances between 12 and 14.5 ppm, which indicate the formation of a hairpin structure, were observed for pre-miRNA-1229_WT FL, these resonances being absent in pre-miRNA-1229_WT GQ (compare FIGS. 2A and 3A). The broadness of these resonances could be due to the size of the RNA investigated, but it could also indicate possible exchange between different conformations. Sharper resonances on a broad envelope background were also observed in the range of 10-12 ppm. As discussed above, resonances in the range of 10-12 ppm were assigned to guanine imino protons involved in Hoogsteen base pairs in GQ structures. However, in sequences that cannot form GQ structures, sharper resonances in these regions were assigned to GU wobble base pairs or side-by-side GG/GA base pairs, while broader resonances were assigned to unpaired G or U imino protons located in hairpin loops. Moreover, although Watson-Crick imino protons are observed typically in the range of 12-14.5 ppm, there are instances where the imino proton of a guanine involved in a GC base pair immediate to an internal loop could give rise to a resonance around 11.9 ppm. The predicted extended hairpin structure of pre-miRNA-1229_WT FL (FIG. 1A) contained internal loops where GG or GA base pairs could form, unpaired G and U residues in the terminal loop, as well as GC Watson-Crick base pairs immediately adjacent to internal loops, all of which could give rise to the sharper resonances observed in the 10-12 ppm region. The presence of a broader envelope resonance centered around 11 ppm, visible especially upon addition of higher KCl concentrations, suggested also the presence of a GQ structure (FIG. 3A). However, the GQ structure signatures become clearly visible only once the sample was annealed in the presence of 150 mM KCl, as the intensity of the broad resonance around 11 ppm increased with the concomitant decrease of the resonances in the Watson-Crick imino proton region (FIG. 3A, top spectrum). These results indicate that pre-miRNA-1229_WT FL formed a GQ structure coexisting in equilibrium with a hairpin structure, with the GQ structure being stabilized by annealing the RNA in the presence of KCl. With respect to FIGS. 3A-3D, biophysical characterization of the full-length pre-miRNA-1229_WT FL sequence is shown. FIGS. 3A and 3B show $^{1}$H NMR spectra and CD spectra, respectively, at various KCl concentrations in 10 mM cacodylic acid, pH 6.5, revealing an equilibrium between hairpin and GQ structures after annealing the RNA in 150 mM KCl. The UV thermal denaturation hypochromic transition shown in FIG. 3C at 10 μM RNA in 100 mM KCl was fit using Equation (1) (Materials and Methods), to determine a $T_m$ of ~85° C. Nondenaturing gel electrophoresis shown in FIG. 3D is visualized by UV shadow (left panel) and stained with the GQ-specific NMM dye, revealing the formation of multiple GQ structures.

CD spectroscopy experiments were performed for pre-miRNA-1229_WT FL at varying KCl concentrations in the range of 0-150 mM (FIG. 3B), revealing a positive band at ~265 nm, a negative band at ~235 nm, an intense negative band at 210 nm, and a small negative CD between 290 and 300 nm. These bands, which did not change significantly with the KCl titrations, were consistent with the presence of both a hairpin and a GQ structure coexisting in equilibrium. Additionally, consistent with $^{1}$H NMR spectroscopy results (FIG. 3A, top spectrum), only when the sample was annealed at 95° C. in 150 mM KCl was a noticeable difference observed in the CD spectrum, with an increase in the intensity of the positive band at ~265 nm and a decrease in the intensity of the negative band at ~210 nm, indicating a shift of the equilibrium towards the GQ structure.

UV thermal denaturation experiments were performed at 295 nm to determine the stability of the GQ structure formed within the pre-miRNA-1229_WT FL sequence. A hypochromic transition corresponding to GQ structure dissociation was observed between 79 and 95° C., and a hyperchromic transition was observed between 46 and 79° C., corresponding to the hairpin structure dissociation (FIG. 3C). These experiments were performed in the presence of 100 mM KCl, as at 150 mM KCl, the GQ structure was too stable, resulting in an incomplete hypochromic transition (data not shown). The GQ dissociation transition was fit using Equation (1) (Materials and Methods) (FIG. 3C) to determine a $T_m$ of ~85° C.

To further characterize the equilibrium between the hairpin and GQ structures in pre-miRNA-1229_WT FL, 15% nondenaturing gel electrophoresis at various concentrations of KCl (FIG. 3D) was performed. When the gel was visualized by UV shadowing, a single main band was evident at all concentrations of KCl, with very faint upper bands also apparent (FIG. 3D, left panel). When the gel was stained in the GQ-specific NMM dye, the main band stained, but multiple upper bands and a lower band also became clearly visible (FIG. 3D, right panel), indicating the presence of multiple GQ structure conformations due to the presence of six G-tracts in the sequence (FIG. TA), as well as possible stacking interactions between GQ structures.

The results from these biophysical characterization studies showed that GQ structures were retained in the context of the full-length pre-miRNA-1229_WT FL sequence, which coexist in equilibrium with the canonical extended hairpin structure. Additionally, while the GQ structure can form in the absence of $K^+$ ions, it was stabilized by annealing the RNA in the presence of 150 mM KCl (FIG. 3A).

To monitor the equilibrium between the GQ and hairpin structures in ionic conditions closer to physiological conditions, 1 mM $MgCl_2$ was added to the NMR sample previously annealed in the presence of 150 mM KCl (FIG. 4A, bottom spectrum), acquiring time-dependent spectra over the course of 6 days, during which time the sample was incubated at 37° C. (FIG. 4). $Mg^{2+}$ ions stabilize various RNA structures, including hairpins, and this was observed for pre-miRNA-1229_WT FL since the imino proton resonances corresponding to Watson-Crick base pairs became sharper over time (FIG. 4A). However, the broad resonances centered around 11 ppm, corresponding to guanine imino protons engaged in Hoogsteen base pairs in the GQ structure, increased in intensity, suggesting that the equilibrium was shifted towards the GQ structure over time (FIG. 4A and overlay of spectra in FIG. 4B).

These studies together show for the first time that a GQ structure coexists in equilibrium with a hairpin structure within the G-rich pre-miRNA-1229 sequence. GQ structure formation within pre-miRNAs has been previously shown to reduce the levels of mature miRNA production, thus, the results suggest that the GQ structure within pre-miRNA-1229 could provide a fine-tuning control mechanism for the production of mature miRNA-1229. The results of this study have implications for AD, as the mature miRNA-1229 has been shown to regulate the translation of SORL1, a protein whose downregulated expression has been shown to result in APP being sorted into Aβ-generating pathways. Thus, the GQ structure characterized within pre-miRNA-1229 could potentially become a therapeutic target in AD, as molecules that stabilize it could ultimately reduce the levels of mature miRNA-1229. FIG. 4A shows time-dependent $^1H$ NMR spectra of full-length pre-miRNA-1229_WT FL in the presence of 150 mM KCl and 1 mM $MgCl_2$. After approximately 140 h, the GQ structure is the preferred structure, as indicated by the increased intensity of the imino proton resonances corresponding to Hoogsteen base pairs in the GQ structure compared to those assigned to Watson-Crick imino proton resonances. An overlay of the spectra is shown in FIG. 4B.

Example 3: The GQ Structure Formed by the G-Rich Region of Pre-miRNA-1229 Is Retained in the AD-Associated rs2291418 Variant Ghanbari et al. (*Sci. Rep.* 2016, 6: 28387) demonstrated not only that miRNA-1229 is implicated in AD by regulating the translation of SORL1, but also that the pre-miRNA-1229 variant rs2291418 (cytosine to uracil in the RNA, indicated by arrows in FIGS. 1B-1C), which results in increased levels of mature miRNA-1229-3p, is associated with AD. Given that the rs2291418 SNP is located within the G-rich region of pre-miRNA-1229 (arrows in FIGS. 1A-1C), the present inventors hypothesized that this variant could potentially change the equilibrium between the GQ and hairpin structures within pre-miRNA-1229 and consequently, dysregulate the control of the mature miRNA-1229 production. Similar to investigation of the truncated 42-nt pre-miRNA-1229 WT GQ, a truncated pre-miRNA-1229_SNP sequence (named pre-miRNA-1229_SNP GQ, Table 1) was generated and characterized using similar biophysical techniques. $^1H$ NMR spectroscopy experiments of pre-miRNA-1229_SNP GQ revealed broad imino proton resonances centered around 11 ppm which increased in intensity as KCl was titrated in the sample (FIG. 5A), indicative of the formation of a GQ structure that is stabilized by $K^+$ ions. No resonances were observed in the region corresponding to Watson-Crick imino protons as was observed for the truncated WT sequence (compare FIGS. 2A and 5A), suggesting that the rs2291418 SNP disrupted the loop-loop interactions that were occurring within the wild-type sequence. FIGS. 5A-5D show biophysical characterization of the truncated pre-miRNA-1229_SNP GQ sequence. FIGS. 5A and 5B show $^1H$ NMR spectra and CD spectra, respectively, at various KCl concentrations in 10 mM cacodylic acid, pH 6.5, demonstrating the formation of a GQ structure. The UV thermal denaturation hypochromic transition shown in FIG. 5C at 10 μM RNA in 150 mM KCl was fit using Equation (1) (Materials and Methods), to determine a $T_m$ of ~78° C. The $T_m$ values plotted as a function of the RNA concentration shown in FIG. 5D revealed that an intramolecular GQ structure is formed. Nondenaturing gel electrophoresis shown in FIG. 5E, visualized by UV shadow (left panel) and stained with the GQ-specific NMM dye (right panel), reveals the formation of a GQ structure at all KCl concentrations.

The directionality of the GQ structure formed by pre-miRNA-1229_SNP GQ was analyzed using CD spectroscopy (FIG. 5B), while titrating KCl in the range of 0-150 mM. The signature positive band at ~265 nm and negative band at ~240 nm corresponding to a parallel GQ were evident at all concentrations of KCl, and a noticeable increase in band intensity was observed upon the addition of 10 mM KCl, indicating further stabilization of this GQ structure by $K^+$ ions and consistent with the $^1H$ NMR spectroscopy results (FIG. 5A). These results differed from the pre-miRNA-1229_WT GQ results (compare FIGS. 2B and 5B), as the GQ formed within that sequence was stable even in the absence of $K^+$ ions. Moreover, the small intensity negative band at 210 nm observed for pre-miRNA-1229 WT GQ (FIG. 2B) was absent from the spectra of pre-miRNA-1229_SNP GQ (FIG. 5B), suggesting the absence of loop-loop interactions within the GQ structure formed within this sequence and consistent with the $^1H$ NMR spectroscopy results.

To determine the stability of the GQ structure formed by pre-miRNA-1229_SNP GQ, UV thermal denaturation experiments were performed at a fixed KCl concentration of 150 mM and RNA concentrations in the range of 5-50 μM. At all RNA concentrations, a single hypochromic transition corresponding to GQ structure dissociation was observed which was fit (FIG. 5C) using Equation (1) (Materials and Methods) to determine an average $T_m$ of ~78° C. As with the wild-type pre-miRNA-1229_WT GQ sequence, the GQ melting temperatures did not depend on the RNA concentration, indicating that pre-miRNA-1229_SNP GQ formed an intramolecular GQ structure (FIG. 5D). The $T_m$ values of the GQ structures formed by the wild-type and SNP truncated sequences of pre-miRNA-1229 were almost identical at 150 mM KCl, suggesting that the additional stabilization observed for the GQ structure formed by pre-miRNA-1229_WT GQ originated from loop-loop interactions, potentially involving the mutated cytosine to uracil residue, interactions that were absent in pre-miRNA-1229_SNP GQ.

Then, 20% nondenaturing gel electrophoresis (FIG. 5E) was performed at various KCl concentrations in the range of 0-150 mM. At each KCl concentration, a single main band was evident when the gel was visualized by UV shadowing (FIG. 5E, left panel). This band was also present when the gel was stained by NMM (FIG. 5E, right panel), indicating that it corresponded to a GQ structure. An additional lower band was also present in the NMM stained gel, indicating the formation of alternative GQ structures, as was seen with pre-miRNA-1229_WT GQ (FIG. 2E).

Taken together, these results show that a parallel, intramolecular GQ structure formed within pre-miRNA-1229_SNP GQ, but this structure lacked the loop-loop interactions that stabilize the GQ structure formed within the wild-type pre-miRNA-1229_WT GQ sequence.

Example 4: The AD-Associated rs2291418 Mutation within the Full-Length Pre-miRNA-1229 Shifts the Equilibrium from the GQ Structure to the Extended Hairpin Structure To determine if the GQ structure was retained in the full-length rs2291418 pre-miRNA-1229 sequence, the full 70-nucleotide sequence (named pre-miRNA-1229_SNP FL, Table 1) was characterized. Similar to the full-length WT sequence, $^1$H NMR spectroscopy experiments (FIG. 6A, bottom spectrum) revealed imino proton resonances in both the GQ and Watson-Crick imino proton regions. The resonances in the Watson-Crick region were well defined and sharper than those observed for pre-miRNA-1229_WT FL at all concentrations (compare FIGS. 3A and 6A), indicating a stable hairpin structure formation. There was also observed sharper resonances in the 10-12 ppm region (FIG. 6A) that could have originated from GG base pairs within internal loops, unpaired G and U residues present in the terminal loop, as well as GC Watson-Crick base pairs adjacent to internal loops of pre-miRNA-1229_SNP FL (FIG. 1B). However, in contrast to the spectra of pre-miRNA-1229_WT FL, these resonances had a completely flat baseline even at 150 mM KCl concentrations. Only when the sample was annealed at 150 mM KCl did broad envelope resonances appear clearly in the 10-12 pm region, with the concomitant decrease in intensity of the Watson-Crick resonances, indicating that a GQ structure did not stably form in pre-miRNA-1229_SNP FL until the sample was annealed in the presence of $K^+$ ions.

To determine the directionality of the GQ structure formed in pre-miRNA-1229_SNP FL, CD spectroscopy experiments were performed at KCl concentrations in the range of 0-150 mM (FIG. 6B). A positive band at ~265 nm, a negative band at ~235 nm, a negative band at –210 nm, and a small negative CD between 290 and 300 nm were observed, consistent with the presence of a hairpin structure. The presence of a GQ structure was not ruled out based solely on the CD data since the signature bands of a parallel GQ structure overlap to some extent with those of an A-type hairpin structure. However, the annealing of the sample in the presence of 150 mM KCl caused an increase of the intensity of the positive band at ~265 nm with a concomitant decrease of the intensity of the negative band at ~210 nm and a shift of the negative band from 235 to 240 nm, indicating the formation of a stable GQ structure which coexisted with the hairpin structure. These results are similar to those from the $^1$H NMR spectroscopy experiments which showed that a stable GQ structure did not form in pre-miRNA-1229_SNP FL until the sample was annealed in the presence of $K^+$ ions.

UV thermal denaturation experiments were performed (FIG. 6C) at 100 mM KCl to determine the stability of the GQ structure formed within pre-miRNA-1229_SNP FL. Similar to pre-miRNA-1229_WT FL, a hyperchromic transition corresponding to hairpin dissociation and a hypochromic transition corresponding to the GQ structure unfolding were observed (FIG. 6C, left). The hypochromic transition was fitted with Equation (1) (Materials and Methods) to determine a $T_m$ of ~86° C. (FIG. 6C, right), which was comparable with the $T_m$ of the GQ structure formed by pre-miRNA-1229_WT FL. FIGS. 6A-6D shown biophysical characterization of the full-length pre-miRNA-1229_SNP FL sequence. FIGS. 6A and 6B show $^1$H NMR spectra and CD spectra, respectively, at various KCl concentrations in 10 mM cacodylic acid, pH 6.5 reveal an equilibrium between hairpin and GQ structures after annealing the RNA in 150 mM KCl. UV thermal denaturation hypochromic transition shown in FIG. 6C at 10 μM RNA in 100 mM KCl was fit using Equation (1) (Materials and Methods), to determine a $T_m$ of ~86° C. Nondenaturing gel electrophoresis shown in FIG. 6D visualized by UV shadow (left panel) and stained with the GQ-specific NMM dye (right panel), reveals the formation of multiple GQ structures as well as a hairpin structure.

A 15% nondenaturing gel electrophoresis was performed at various KCl concentrations in the range of 0-150 mM (FIG. 6D). When the gel was visualized by UV shadowing (FIG. 6D, left panel), a single main band was observed at 0 mM KCl, whereas a second, upper band was clearly visible with the addition of just 5 mM KCl (compare FIG. 6D lanes 1 and 2). As the concentration of KCl in the sample increased, the primary band seen at 0 mM KCl decreased in intensity, indicating an equilibrium between competing structures. When the gel was stained in NMM (FIG. 6D, right panel), the main band clearly observed at 0 mM KCl by UV shadowing stained faintly, indicating that a GQ structure formed. Since all the RNA samples were annealed prior to their loading on the gel, the annealing could have promoted formation of the GQ structures even at 0 mM KCl. Upon the addition of increasing KCl concentrations, the additional upper band observed when the gel was visualized by UV shadowing also stained in NMM, indicating that it originated from a GQ structure (FIG. 6E, right panel). Additional fainter upper bands and a lower band were also apparent in the NMM stained gel, indicating alternative GQ structures and/or GQ stacking interactions, as was observed with pre-miRNA-1229 WT FL (FIG. 3E, right panel). These results confirmed that pre-miRNA-1229_SNP FL exists in equilibrium between a hairpin and GQ structures with the GQ conformations being stabilized when the RNA was annealed at 150 mM KCl.

To monitor the equilibrium between the GQ and hairpin structure in pre-miRNA-1229_SNP FL in conditions that stabilize the hairpin conformation, time-dependent $^1$H NMR spectroscopy experiments were performed in the presence of 150 mM KCl and 1 mM $MgCl_2$ (FIG. 7A), while the sample was incubated at 37° C. In the presence of $Mg^2$ ions, there was a stabilization of the hairpin structure reflected by sharper Watson-Crick imino proton resonances between 12 and 14.5 pm, however, the GQ broad imino proton resonances that centered around 11 ppm decreased over time (FIG. 7A and overlay of spectra in FIG. 7B), indicating that the equilibrium shifted towards the hairpin structure. In contrast, the time-dependent $^1$H NMR spectroscopy experiments for pre-miRNA-1229_WT FL (compare to FIG. 4) indicated that the equilibrium shifted over time towards the GQ structure. FIG. 7A shows time-dependent NMR spectra of full-length pre-miRNA-1229_SNP FL in the presence of 150 mM KCl and 1 mM $MgCl_2$. After 166 h, the hairpin structure is the preferred structure, as noted by the increased intensity of the Watson-Crick imino proton resonances compared to the decreased intensity of the imino proton resonances assigned to Hoogsteen base pairs in the GQ structure. An overlay of the spectra is shown in FIG. 7B.

The results indicate that while a hairpin and GQ structure coexist within the pre-miRNA-1229_SNP FL sequence, the hairpin structure is ultimately favored in the rs2291418 AD-associated variant.

It was proposed that the observed increased levels of miRNA-1229-3p in the AD-associated rs2291418 SNP within pre-miRNA-1229 are due to the stabilization of the hairpin structure by the SNP. The predicted value of the minimum free energy of the SNP hairpin was $\Delta G°=-36.10$ kcal/mol, whereas that of the WT was $\Delta G°=-31.90$ kcal/mol. However, herein, when the pre-miRNA-1229_WT FL and pre-miRNA-1229_SNP FL were folded with the RNA-Structure software (FIGS. 1A,C), the two hairpin structures were predicted to have free energies of $\Delta G°=-36.0$ kcal/mol and $\Delta G°=-36.7$ kcal/mol, respectively, which differed only by 0.7 kcal/mol. Both of the wild-type and SNP pre-miRNA-1229 sequences formed GQ structures that coexisted in equilibrium with the canonical extended hairpin structure, and the GQ structure was destabilized in the rs2291418 variant, potentially due to the lack of loop-loop interactions, resulting in a shift in equilibrium towards the hairpin structure.

Investigating the molecular pathways and key mechanistic steps involved in AD pathogenesis is vital for the development of therapeutic interventions for the disease. Research in the field has shifted focus to the involvement of noncoding miRNAs in AD due to their contributions in regulating gene expression, Aβ and tau protein maintenance, inflammation, and cell death. A recent study suggested that miRNA-107 plays a neuroprotective role in AD progression and that its expression levels are reduced in an AD-induced AD model.

Furthermore, a mechanism has been proposed in which the long noncoding RNA (lncRNA) NEAT1 binds to miRNA-107, leading to this downregulation. In this study, pre-miRNA-1229 was investigated due to the association of the rs2291418 variant with AD and subsequent upregulation of miRNA-1229-3p production, and a GQ structure present in both the wild-type and rs2291418 variant that is a new therapeutic target in AD was identified.

These results have implications beyond the AD context, as multiple other studies have determined that the upregulation of miRNA-1229 can be associated with various other diseases. Expression levels of miRNA-1229 were found to be correlated with increased severity of coronary artery calcification and increased tumor size in colorectal cancer. Furthermore, miRNA-1229 overexpression has been proposed to promote cell proliferation and tumorigenicity in breast cancer.

Thus, a mechanism in which the pre-miRNA-1229 equilibrium between GQ and extended hairpin structures is altered in the rs2291418 variant is proposed, potentially explaining the increased mature miRNA-1229-3p production observed in the AD-linked variant. Based on the results, RNA structure can potentially have downstream effects in disease pathogenesis, and GQ structures such as that found in pre-miRNA-1229, could ultimately be therapeutically targeted for intervention purposes.

Collectively, the biophysical characterization experiments performed in this study determined that pre-miRNA-1229 formed a GQ structure which coexisted in equilibrium with an extended hairpin structure. Described herein are G-rich pre-miRNA sequences shown to form GQ structures that could interfere with their processing by Dicer and the production of mature miRNA, ultimately providing a fine-tuned mechanism for regulating translation. Furthermore, the results show that while in the WT pre-miRNA-1229 the GQ structure is preferred, in the AD-associated rs2291418 pre-miRNA-1229 variant the equilibrium is shifted towards the extended hairpin structure which can be processed by Dicer, possibly explaining the observed increased production of the mature miRNA-1229-3p in this variant. The results elucidate a role of RNA secondary structure equilibrium in the AD pathogenesis and warrant therapeutic targeting of GQ structures.

Example 5: Stabilization of Wild Type Pre-miRNA-1229 or the rs2291418 Variant The GQ structure formed by either the wild type pre-miRNA-1229 or by the rs2291418 variant (cytosine to uracil in the RNA) are targeted for stabilization over the hairpin structure with which it is in equilibrium. This results in producing less of the mature miRNA-1229, as when folded in the GQ structure, pre-miRNA-1229 cannot be processed by Dicer.

GQ structures can be stabilized by modified PNAs (gamma PNAs) that are complementary to and target flanking sequences (for specificity) and two of the G repeats that are involved in the GQ formation. Thus, to target the pre-miRNA-1229 GQ structure the following PNA sequences are used (the bolded C repeats target the G repeats forming the GQ):

1. PNA1 GQ-1229 $H_2N$-LysAGCCCACGCUCUCCCCCAAA-H (SEQ ID NO: 5; targets G repeats 3 and 4)
2. PNA2 GQ-1229 $H_2N$-LysUGAACCCCAGCCCACGCUCU-H (SEQ ID NO: 6; targets G repeats 4 and 5)
3. PNA3 GQ-1229 $H_2N$-LysGGGUGUCCCUGAACCCCAGC-H (SEQ ID NO: 7; targets G repeats 5 and 6)

The pre-miRNA-1229 GQ structure is also targeted with 2'-deoxy 2'-fluoroarabino (2'-FANA) oligonucleotides comprising the following sequences:

AGCCCACGCUCUCCCCCAAA (SEQ ID NO: 8)

UGAACCCCAGCCCACGCUCU; (SEQ ID NO: 9)

and

GGGUGUCCCUGAACCCCAGC. (SEQ ID NO: 10)

The FANA oligonucleotides have the ability to penetrate the cell membrane by gymnosis, which is the process by which antisense oligodeoxynucleotides are delivered to cells, in the absence of any carriers or conjugation, making them excellent drug candidates.

Additionally, the GQ structure formed by either the wild type pre-miRNA-1229 or by the rs2291418 variant are targeted by small molecules which are identified through using a small molecule microarray (SMM) high throughput screening platform.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

The invention claimed is:

1. An agent that binds to a wild type or variant pre-miRNA-1229 comprising a G-quadruplex (GQ) structure, wherein binding of the agent to the wild type or variant pre-miRNA-1229 stabilizes the GQ structure of the wild type or variant pre-miRNA-1229,wherein the agent consists of an oligonucleotide sequence comprising 2'-deoxy 2'-fluoroarabino oligonucleotides consisting of: GGGUGUCC-CUGAACCCCAGC (SEQ ID NO:10), wherein the variant is rs2291418.

2. A composition comprising the agent of claim 1.

* * * * *

SEQUENCE LISTING

<160> NUMBER OF SEQ ID NOS: 10

<210> SEQ ID NO 1
<211> LENGTH: 42
<212> TYPE: RNA
<213> ORGANISM: artificial sequence
<220> FEATURE:
<223> OTHER INFORMATION: pre-miRNA-1229_WT GQ

<400> SEQUENCE: 1 ggguagggu ugggggagag cgugggcugg gguucaggga ca 42

<210> SEQ ID NO 2
<211> LENGTH: 70
<212> TYPE: RNA
<213> ORGANISM: artificial sequence
<220> FEATURE:
<223> OTHER INFORMATION: pre-miRNA-1229_WT FL

<400> SEQUENCE: 2
gguggguagg guuuggggga gagcgugggc uggggguucag ggacacccuc ucaccacugc 60
ccucccacag 70

<210> SEQ ID NO 3
<211> LENGTH: 42
<212> TYPE: RNA
<213> ORGANISM: artificial sequence
<220> FEATURE:
<223> OTHER INFORMATION: pre-miRNA-1229_SNP GQ

<400> SEQUENCE: 3 ggguagggu ugggggagag ugugggcugg gguucaggga ca 42

<210> SEQ ID NO 4
<211> LENGTH: 70
<212> TYPE: RNA
<213> ORGANISM: artificial sequence
<220> FEATURE:
<223> OTHER INFORMATION: pre-miRNA-1229_SNP FL

<400> SEQUENCE: 4
gguggguagg guuuggggga gagugugggc uggggguucag ggacacccuc ucaccacugc 60
ccucccacag 70

<210> SEQ ID NO 5
<211> LENGTH: 20
<212> TYPE: RNA
<213> ORGANISM: artificial sequence
<220> FEATURE:
<223> OTHER INFORMATION: synthetic RNP

<400> SEQUENCE: 5
agcccacgcu cucccccaaa 20

<210> SEQ ID NO 6
<211> LENGTH: 20
<212> TYPE: RNA
<213> ORGANISM: artificial sequence
<220> FEATURE:
<223> OTHER INFORMATION: synthetic RNP

<400> SEQUENCE: 6
ugaaccccag cccacgcucu 20

```
<210> SEQ ID NO 7
<211> LENGTH: 20
<212> TYPE: RNA
<213> ORGANISM: artificial sequence
<220> FEATURE:
<223> OTHER INFORMATION: synthetic RNP

<400> SEQUENCE: 7

ggguguccu gaaccccagc                                               20


<210> SEQ ID NO 8
<211> LENGTH: 20
<212> TYPE: RNA
<213> ORGANISM: artificial sequence
<220> FEATURE:
<223> OTHER INFORMATION: synthetic 2'-FANA oligonucleotide

<400> SEQUENCE: 8

agcccacgcu cucccccaaa                                              20


<210> SEQ ID NO 9
<211> LENGTH: 20
<212> TYPE: RNA
<213> ORGANISM: artificial sequence
<220> FEATURE:
<223> OTHER INFORMATION: synthetic 2'-FANA oligonucleotide

<400> SEQUENCE: 9

ugaaccccag cccacgcucu                                              20


<210> SEQ ID NO 10
<211> LENGTH: 20
<212> TYPE: RNA
<213> ORGANISM: artificial sequence
<220> FEATURE:
<223> OTHER INFORMATION: synthetic 2'-FANA oligonucleotide

<400> SEQUENCE: 10

ggguguccu gaaccccagc                                               20
```